(12) United States Patent
Gabos et al.

(10) Patent No.: US 7,655,664 B2
(45) Date of Patent: Feb. 2, 2010

(54) HYDANTOIN DERIVATIVES AS METALLOPROTEINASE INHIBITORS

(75) Inventors: Balint Gabos, Lund (SE); Michael Lundkvist, Lund (SE); Magnus Munck Af Rosenschold, Lund (SE); Igor Shamovsky, Lund (SE); Pavol Zlatoidsky, Lund (SE)

(73) Assignee: AstraZeneca AB (SE)

( * ) Notice: Subject to any disclaimer, the term of this patent is extended or adjusted under 35 U.S.C. 154(b) by 237 days.

(21) Appl. No.: 11/721,586

(22) PCT Filed: Dec. 14, 2005

(86) PCT No.: PCT/SE2005/001917

§ 371 (c)(1),
(2), (4) Date: Jun. 13, 2007

(87) PCT Pub. No.: WO2006/065215

PCT Pub. Date: Jun. 22, 2006

(65) Prior Publication Data

US 2008/0293743 A1    Nov. 27, 2008

(30) Foreign Application Priority Data

Dec. 17, 2004  (SE)  .................................. 0403085

(51) Int. Cl.
C07D 401/14  (2006.01)
A61K 31/444  (2006.01)

(52) U.S. Cl. ....................... 514/256; 544/333; 514/300; 514/309; 546/122; 546/141

(58) Field of Classification Search ................. 544/333; 546/122, 141; 514/256, 300, 309
See application file for complete search history.

(56) References Cited

U.S. PATENT DOCUMENTS

| | | | |
|---|---|---|---|
| 2,327,890 A | 8/1943 | Henze | |
| 2,745,875 A | 5/1956 | Ehrhart et al | |
| 3,452,040 A | 6/1969 | Langis | |
| 3,529,019 A | 9/1970 | Suh et al. | |
| 3,849,574 A | 11/1974 | Suh et al. | |
| 4,241,073 A | 12/1980 | Jamieson et al. | |
| 4,315,031 A | 2/1982 | Vincent et al. | |
| 4,983,771 A | 1/1991 | Bryker et al. | |
| 5,068,187 A | 11/1991 | Takeichi et al. | |
| 5,246,943 A | 9/1993 | Blankley et al. | |
| 5,308,853 A | 5/1994 | Hodges et al. | |
| 5,521,187 A | 5/1996 | Freyne et al. | |
| 5,804,593 A | 9/1998 | Warpehoski et al. | |
| 5,919,790 A | 7/1999 | Allen et al. | |
| 5,955,435 A | 9/1999 | Baxter et al. | |
| 6,046,214 A | 4/2000 | Kristiansen et al. | |
| 6,048,841 A | 4/2000 | Baxter et al. | |
| 6,114,361 A | 9/2000 | Robinson et al. | |
| 6,159,995 A | 12/2000 | Thorwart et al. | |
| 6,166,041 A | 12/2000 | Cavalla et al. | |
| 6,218,418 B1 | 4/2001 | Pevarello et al. | |
| 6,268,379 B1 | 7/2001 | Xue et al. | |
| 6,277,987 B1 | 8/2001 | Kukkola et al. | |
| 6,291,685 B1 | 9/2001 | Junghans et al. | |
| 6,329,418 B1 | 12/2001 | Cheng et al. | |
| 6,339,101 B1 | 1/2002 | Ross et al. | |
| 6,340,691 B1 | 1/2002 | Levin et al. | |
| 6,429,213 B1 | 8/2002 | Xue et al. | |
| 6,890,915 B2 | 5/2005 | Sheppeck et al. | |
| 6,906,053 B2 | 6/2005 | Sheppeck et al. | |
| 7,078,424 B2 | 7/2006 | Hamilton et al. | |
| 7,132,434 B2 | 11/2006 | Eriksson et al. | |
| 7,354,940 B2 | 4/2008 | Henriksson et al. | |
| 7,368,465 B2 | 5/2008 | Eriksson et al. | |
| 7,427,631 B2 | 9/2008 | Eriksson et al. | |
| 2002/0006920 A1 | 1/2002 | Robinson et al. | |
| 2002/0028835 A1 | 3/2002 | Hu et al. | |
| 2002/0065219 A1 | 5/2002 | Naidu et al. | |
| 2002/0091107 A1 | 7/2002 | Madar et al. | |
| 2003/0130273 A1 | 7/2003 | Sheppeck et al. | |
| 2004/0044215 A1 | 3/2004 | Alcade et al. | |
| 2004/0106659 A1 | 6/2004 | Af Rosenschold | |
| 2004/0110809 A1 | 6/2004 | Lepisto et al. | |
| 2004/0116486 A1 | 6/2004 | Lepisto et al. | |
| 2004/0127528 A1 | 7/2004 | Eriksson et al. | |
| 2004/0138276 A1 | 7/2004 | Eriksson et al. | |

(Continued)

FOREIGN PATENT DOCUMENTS

EP    0175312    3/1986

(Continued)

OTHER PUBLICATIONS

Rasmussen et al., Matrix Metalloproteinase Inhibition as a novel anticancer strategy, Pharmacol. Ther., vol. 75, No. 1, pp. 69-75, 1997.*

Avgeropoulos et al., New Treatment Strategies for Malignant Gliomas, The Oncologist, 4:209-224, 1999.*

Simone, Oncology: Introduction, Cecil Textbook of Medicine, 20th Edition, vol. 1, pp. 1004-1010, 1996.*

(Continued)

*Primary Examiner*—Deepak Rao
(74) *Attorney, Agent, or Firm*—Fish & Richardson P.C.

(57) ABSTRACT

The invention provides compounds of formula (I): wherein $R^1$, $R^2$, A, $A^1$ and B are as defined in the specification; processes for their preparation; pharmaceutical compositions containing them; a process for preparing the pharmaceutical compositions; and their use in therapy. The compounds are useful as MMP inhibitors.

(I)

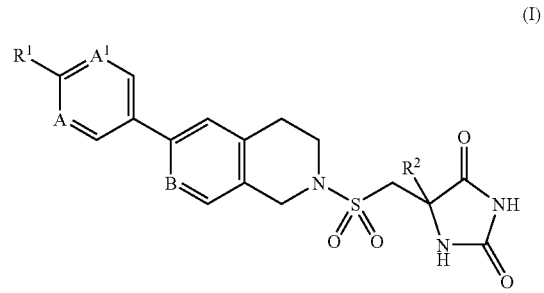

9 Claims, No Drawings

U.S. PATENT DOCUMENTS

| | | |
|---|---|---|
| 2004/0147573 A1 | 7/2004 | Eriksson et al. |
| 2004/0152697 A1 | 8/2004 | Chan et al. |
| 2004/0209874 A1 | 10/2004 | Sheppeck et al. |
| 2004/0266832 A1 | 12/2004 | Li et al. |
| 2005/0019994 A1 | 1/2005 | Chang |
| 2005/0026990 A1 | 2/2005 | Eriksson et al. |
| 2005/0171096 A1 | 8/2005 | Sheppeck et al. |
| 2005/0256176 A1 | 11/2005 | Burrows et al. |
| 2006/0063818 A1 | 3/2006 | Burrows et al. |
| 2006/0276524 A1 | 12/2006 | Henriksson et al. |
| 2008/0004317 A1 | 1/2008 | Gabos et al. |
| 2008/0032997 A1 | 2/2008 | Gabos et al. |
| 2008/0064710 A1 | 3/2008 | Gabos et al. |
| 2008/0171882 A1 | 7/2008 | Eriksson et al. |
| 2008/0221139 A1 | 9/2008 | Chapman et al. |
| 2008/0262045 A1 | 10/2008 | Eriksson et al. |
| 2008/0293743 A1 | 11/2008 | Gabos et al. |
| 2008/0306065 A1 | 12/2008 | Eriksson et al. |
| 2009/0054659 A1 | 2/2009 | Cornwall et al. |

FOREIGN PATENT DOCUMENTS

| | | |
|---|---|---|
| EP | 212617 | 8/1986 |
| EP | 0255390 | 2/1988 |
| EP | 0442584 | 8/1991 |
| EP | 0486280 | 11/1991 |
| EP | 0580210 | 1/1994 |
| EP | 0640594 A1 | 3/1995 |
| EP | 0709375 | 10/1995 |
| EP | 0909754 | 4/1999 |
| EP | 1149843 A1 | 10/2001 |
| EP | 1191024 | 3/2002 |
| EP | 1117616 | 4/2003 |
| EP | 02 74 1724 | 3/2004 |
| EP | 1550725 | 7/2005 |
| WO | WO 92/01062 | 1/1992 |
| WO | WO 95/14025 | 5/1995 |
| WO | WO 96/21640 | 7/1996 |
| WO | WO 96/27583 | 9/1996 |
| WO | WO 98/50359 | 5/1998 |
| WO | WO 99/06361 | 2/1999 |
| WO | WO 99/42443 | 2/1999 |
| WO | WO 99/24399 | 5/1999 |
| WO | WO 00/09103 | 8/1999 |
| WO | WO 00/35886 | 12/1999 |
| WO | WO 99/62880 | 12/1999 |
| WO | WO 00/12477 | 3/2000 |
| WO | WO 00/12478 | 3/2000 |
| WO | WO 00/40577 | 7/2000 |
| WO | WO00/44770 | 8/2000 |
| WO | WO 00/75106 | 12/2000 |
| WO | WO 01/05756 | 1/2001 |
| WO | WO 01/12189 | 2/2001 |
| WO | WO 01/22363 | 3/2001 |
| WO | WO 01/34573 | 5/2001 |
| WO | WO 02/06232 | 1/2002 |
| WO | WO 02/14262 | 2/2002 |
| WO | WO 02/14354 | 2/2002 |
| WO | WO 02/20515 | 2/2002 |
| WO | WO 02/074748 | 9/2002 |
| WO | WO 02/074749 | 9/2002 |
| WO | WO 02/074750 | 9/2002 |
| WO | WO 02/074751 | 9/2002 |
| WO | WO 02/074752 | 9/2002 |
| WO | WO 02/074767 | 9/2002 |
| WO | WO 02/096426 | 12/2002 |
| WO | WO 03/040098 | 5/2003 |
| WO | WO 03/087057 | 10/2003 |
| WO | WO 03/093260 | 11/2003 |
| WO | WO 03/094919 | 11/2003 |
| WO | WO 2004/020415 | 3/2004 |
| WO | WO 2004/024060 | 3/2004 |
| WO | WO 2004/024698 | 3/2004 |
| WO | WO 2004/024715 | 3/2004 |
| WO | WO 2004/024718 | 3/2004 |
| WO | WO 2004/024721 | 3/2004 |
| WO | WO 2004/033632 | 4/2004 |
| WO | WO 2004/108086 | 12/2004 |
| WO | WO2006/004532 | 1/2006 |
| WO | WO2006/004533 | 1/2006 |
| WO | WO 2006/065215 | 6/2006 |
| WO | WO 2006/065216 | 6/2006 |
| WO | WO 2006/077387 | 7/2006 |
| WO | WO 2007/106021 | 9/2007 |
| WO | WO 2007/106022 | 9/2007 |

OTHER PUBLICATIONS

Catterall et al., Drugs in development: bisphosphonates and metalloproteinase inhibitors, Arthritis Research and Therapy, vol. 5, No. 1, pp. 12-24, 2003.*

Visse et al., Matrix Metalloproteinases and Tissue Inhibitors of Metalloproteinases, Circulation Research, 92:827-839, 2003.*

Chambers et al., Changing views of the role of Matrix Metalloproteinases in Metastasis, Journal of the National Cancer Institute, vol. 89, No. 17, Sep. 1997.*

Morris et al., PubMed Abstract (Sequential Steps in Hematogenous Metastasis of Cancer Cells Studied by in vivo Videomicroscopy, Invasion Metastasis, 17:281-296) 1997.*

Aharony et al. "Pharmacological Characterization of a New Class of Nonpeptide Neurokinin A Antagonists that Demonstrate Species Selectivity." J. Pharmacol. Exp. Ther. 274:3 (1995), pp. 1216-1221.

Aimoto et al. "Synthesis of Carriers of Differing Strokes Radius with Activated Acyl Groups for Use as Reagents in Labeling Membrane Proteins." Journal of Biological Chemistry, vol. 256(10), pp. 5134-5143, 1981.

Chemical Abstracts, vol. 65, 1966, Abstract No. 13684 h, M. Lora-Tamayo et al.: "Potential anticancer agents. I. Glutamine sulfonate analogs", & Anales Real Soc. Espan. Fis. Quim (Madrid), Ser. B. 62(2), 173-86.

Croce, P. et al. "Stereoselective aldol addition of a chiral glycine enloate synthon to heteroaromatic aldehydes." Heterocycles, 52:3 (2000) pp. 1337-1344.

Knabe, J. "Razemate und enantiomere basisch substituierter 5-phenylhydantoine." Pharmazie. 52:12 (1997) pp. 912-919.

Bright et al. "Monoclonal Antibodies as Surrogate Receptors in High Throughput Screen for Compounds that Enhance Insulin Sensitivity." Life Sciences. 61:23 (1997), pp. 2305-2315.

Lora-Tamayo et al. "anticancerousos Potenciales." An. Quim. 64:6 (1968), pp. 591-606.

Michaelides et al., "Recent Advances in Matrix Metalloproteinase Inhibitors Research", *Current Pharmaceutical Design* 5:787-819 (1999).

Miyake, Toshiaki et al. "Studies on Glycosylation of erythro-Beta-Hydroxy-L-histidine. A Key Step of Blemycin Total Synthesis." Bull. Chem. Soc. Jpn. 59 (1986), pp. 1387-1395.

Mock et al., "Principles of Hydroxamate Inhibition of Metalloproteases: Carboxypeptidase A", *Biochemistry* 39:13945-13952 (2000).

Nakajima, Riichiro et al. "The utility of 4-(2-thienyl)pyridines as a derivatization reagent for hplc and ce." Analytical Sciences. 7, Supplement 1991, pp. 177-180.

Nicolet, Ben. "Interpretation of the Dyhydration of Acetylglutamic acid by Means of Glutamylthiohydantoin Derivatives." Journal of the American Chemical Society, 1930, pp. 1192-1195.

Owa, Takashi et al. "Man-Designed Bleomycins: Significance of the binding Sites as Enzyme Models and of the Stereochemistry of the Linker Moiety." Tetrahedron. 48:7 (1992) pp. 1193-1208.

Peng, Sean X. "Separation and identification of methods for metalloproteinase inhibitors." Joural of Chromatography B. 764 (2001), pp. 59-80.

Saito, Sei-ichi et al. "A new synthesis of deglyco-bleomycine A2 aiming at the total synthesis of bleomycin." Tetrahedron Letters. 23(5) (1982), pp. 529-532.

STN International, file Caplus, accession No. 1978:424767, Raulais, Daniel J.P., "Synthesis and characterization of phenylthiohydantoin derivatives of amino-acids protected in their sid-chain functions, and their application for monitoring olid-phase peptide synthesis," & Journal of Chemical Research, Synopses (1978), p. 11.

Aigner, T. et al., "Growth Plate Cartilage as Developmental Model in Osteoarthritis Research—Potentials and Limitations", Current Drug Targets, vol. 8, No. 2, pp. 377-385, (2007).

Fujita, Masaki et al., "The pathogenesis of COPD: Lessons Learned from in vivo Animal Models", Med. Sci Monit., vol. 13, No. 2, RA19-24, (2007).

MacFadyen, Robert J., "Can Matrix Metalloproteinase Inhibitors Provide a Realistic Therapy in Cardiovascular Medicine," Current Opinion in Pharmacology, vol. 7, pp. 171-178, (2007).

Rifkin, B.R. et al, "Blocking Periodontal Disease Progression by Inhibiting Tissue-Destructive Enzymes: A Potential Therapeutic Role for Tetracyclines and Their Chemically-Modified Analogs", Periodontol, Aug. 1993 64 (8 Suppl), pp. 819-827.

Wingerchuk, Dean M. et al., "Multiple Sclerosis: Current Pathophysiological Concepts", Biology of Disease, Lab Invest 2001, vol. 81, pp. 263-281, (2001).

STN International, file Caplus, accession No. 1994:299315, Document No. 120:299315, Sakamoto, Shuichi et al., "Preparation of pyridylserine derivatives as psychotropics," WO, A1, 9320053, 19931014, See CAS RN 154696-31-8, 154697-48-0, (1994).

STN International, file Caplus, accession No. 1997:644516, Batty, Craig et al. "Synthesis and exchange reaction of 5-alkyl-2oxo-6-thioxo-1,2,3,6-hexahydropyrimidine-4-carboxylic acids" & Journal of Heterocyclic Chemistry (1997), 34:3, 1355-1367.

STN International, file Caplus, accession No. 2002:640897, Gooding, Owen W. et al. "Use of Statistical Design of Experiments in the Optimization of Amide Synthesis Utilizing Polystryene-Supported N-Hydroxybenzotriazole Resin" & Journal of Combinatorial Chemistry (2002), 4(6), 576-583.

STN International, File Caplus, Caplus accession No. 1968:506154, Doc. No. 69:106154, Lora-Tamayo, J. et al.: "Potential anticancer agents, VI. Sulfonic analogs of aspartic acid", & An. Quim. (1968), 64(6), 591-606, (1968).

STN International, File Caplus, Caplus accession No. 1974:463633, Doc. No. 81:63633, Blaha, Ludvik et al.: "5-Methyl-5-phenoxymethyl-hydantoins", & CS 151744, B, 19731119.

STN International, File Caplus, Caplus accession No. 1988:631020, Doc. No. 109:231020, Mitsui Toatsu Chemicals, Inc.: "Process for the preparation of 5-benzylhydantoins as intermediates for aromatic amino acids": & JP, A2, 63079879, 19880409, (1988).

STN International, File Caplus, Caplus accession No. 1989:173366, Doc. No. 110:173366, Oh, Chang Hyun et al., "Synthesis of new hydantoin-3-acetic acid derivatives", & Bull. Korean Chem. Soc. (1988), 9(4), 231-5.

STN International, File Caplus, Caplus accession No. 1990:138955, Doc. No. 112:138955, Crooks, Peter A. et al.: "Synthesis of 5-benzoyl-5-phenyl-and-5-(Phenylhydroxymethyl)-5-phenylhydantoins as potential anticonvulsants"; & J . Heterocycl. Chem. (1989), 26(4), 1113-17.

Whittaker et al. "Design and Therapeutic Application of Matrix Metalloproteinase Inhibitors." Chem Rev. 99 (1999), pp. 2735-2776.

Banfield, J. E. et al., "Heterocyclic Derivatives of Guanidine. Part V. Reaction of Some Glycidic Esters with Guanidines", *The Journal of The Chemical Society*, 511:2747-2756, (1963).

Belvisi, M. G. et al., "The role of matrix metalloproteinases (MMPs) in the patho-physiology of chronic obstructive pulmonary disease (COPD): a therapeutic role for inhibitors of MMPs?", *Inflammation Research*, 52:95-100, (2003).

Borchers, Michael T. et al., "Acrolein-Induced MUC5ac Expression in Rat Airways", *The American Physiological Society*, 274:L573-L581, (1998).

Carmeliet, Peter, "Proteinases in Cardiovascular Aneurysms and Rupture: Targets for Therapy?", *The Journal of Clinical Investigation*, 105(11):1519-1520, (2000).

Comber, Robert N. et al., "5,5-Disubstituted Hydantoins: Syntheses and Anti-HIV Activity", *J. Med. Chem.*, 35:3567-3572, (1992).

Dahan, Maurice et al., "Expression of Matrix Metalloproteinases in Healthy and Diseased Human Gingiva", *Journal of Clinical Periodontology*, 28:128-136, (2001).

Doherty, Terence M. et al., "Therapeutic Developments in Matrix Metalloproteinase Inhibition", *Expert Opinion Ther. Patents*, 12(5):665-707, (2002).

Elliot, Sarah et al., "The Clinical Potential of Matrix Metalloproteinase Inhibitors in the Rheumatic Disorders", *Drugs & Aging*, 18(2):87-99, (2001).

Gramatica et al., STN International, Hcaplus Database, Columbus, OH, Accession No. 2002:356947, Reg. No. 36734-19-7.

Hautamaki, R. Dean et al., "Requirement for Macrophage Elastase for Cigarette Smoke-Induced Emphysema in Mice", *Science*, 277:2002-2004, (2002).

Lindy, Otso et al., "Matrix Metalloproteinase 13 (Collagenase 3) in Human Rheumatoid Synovium Arthritis Rheumatism," *Arthritis and Rheumatism*, 40(8):1391-1399, (1997).

Mandal, Malay et al., "Clinical Implications of Matrix Metalloproteinases", *Molecular and Cellular Biochemistry*, 252:305-329, (2003).

Pyo, Robert et al., "Targeted Gene Disruption of Matrix Metalloproteinase-9 (Gelatinase B) Suppresses Development of Experimental Abdominal Aortic Aneurysms", *The Journal of Clinical Investigation*, 105(11):1641-1649, (2000).

Rouis, M. et al., "Adenovirus-Mediated Overexpression of Tissue Inhibitor of Metalloproteinase-1 Reduces Atherosclerotic Lesions in Apolipoprotein E-Deficient Mice", *Circulation*, 100:533-540, (1999).

Wernicke, Dirk et al., "Cloning of Collagenase 3 from the Synovial Membrane and Its Expression in Rheumatoid Arthritis and Osteoarthritis", *The Journal of Rheumatology*, 23:590-595, (1996).

Borkakoti, "Matrix metalloprotease inhibitors: design from structure", *Biochemical Society Transactions* 32:17-20 (2004).

Bruce et al., "The effect of marimastat, a metalloprotease inhibitor, on allergen-induced asthmatic hyper-activity", *Toxicol. & Appl. Pharmacol.* 205:126-132 (2005).

Chodosh et al., "Comparative trials of doxycycline versus amoxicillin, cephalexin and enoxacin in bacterial infections in chronic bronchitis and asthma", *Scand. J. Infect. Dis. Suppl.* 53:22-8 (1988).

COPD; http://www.lungsonline.com/copd.html, downloaded Aug. 22, 2008.

Demedts et al., "Elevated MMP-12 protein levels in induced sputum from patients with COPD", *Thorax* 61:196-201 (2006).

Dormán et al., "MMP Inhibitors in Cardiac Diseases: An Update", *Recent Patents on Cardiovascular Drug Discovery* 2:000-000 (2007).

Dorwald, F.Z., "Side Reactions in Organic Synthesis: A Guide to Successful Synthesis Design", 2005, Wiley-VCH Verlag GmbH & Co. KGaA, Weinheim.

Doxycycline hyclate; http://en.wikipedia.org/wiki/Doxycycline_hyclate, downloaded Aug. 22, 2008.

Hirrlinger et al., "Purification and properties of an amidase from Rhodococcus erythropolis MP50 which enantioselectively hydrolyzes 2-arylpropionamides", *J. Bacteriology* 178(12):3501-3507 (1996).

Johnson et al., "Divergent effects of matrix metalloproteinases 3, 7, 9, and 12 on atherosclerotic plaque stability in mouse brachiocephalic arteries", *PNAS* 102(43):15575-15580 (2005).

Kelly et al., "Role of matrix metalloproteinase in asthma", *Current Opinion in Pulmonary Medicine* 9(1):28-33 (2003).

Murphy et al., "Reappraising metalloproteinases in rheumatoid arthritis and osteoarthritis: destruction or repair?", *Nature Clinical Practice Rheumatology* 4:128-135 (2008).

Reisner, "Some α-amino acids containing a sulfonamide group", *J. Am. Chem. Soc.* 78:5102-5104 (1956). CAS abstract and search structure only.

Smith, Michael B., Organic Synthesis Second Edition, 3.9.A Oxidation of sulfur compounds, McGraw-Hill 2002, ISBN-0-07-048242-X, p. 280.

Wikipedia, Matrix metalloproteinase, updated Mar. 09, 2009, <http://en.wikipedia.org/wiki/Matrix_metalloproteinase>, downloaded Mar. 11, 2009.

Wikipedia, Minocycline, updated Feb. 28, 2009, http://en.wikipedia.org/wiki/Minocycline, downloaded Mar. 11, 2009.

* cited by examiner

HYDANTOIN DERIVATIVES AS METALLOPROTEINASE INHIBITORS

CROSS-REFERENCE TO RELATED APPLICATIONS

This application is a national phase application under 35 U.S.C. § 371 of PCT International Application No. PCT/SE2005/001917, filed Dec. 14. 2005, which claims priority to Swedish Application Serial No. 0403085-4, filed Dec. 17, 2004.

The present invention relates to novel hydantoin derivatives, processes for their preparation, pharmaceutical compositions containing them and their use in therapy.

Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354: 1-6. Examples of metalloproteinases include the matrix metalloproteinases (MMPs) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem. J. 321:265-279).

Metalloproteinases have been associated with many diseases or conditions. Inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; asthma; rhinitis; and chronic obstructive pulmonary diseases (COPD).

MMP12, also known as macrophage elastase or metalloelastase, was initially cloned in the mouse by Shapiro et al [1992, Journal of Biological Chemistry 267: 4664] and in man by is the same group in 1995. MMP12 is preferentially expressed in activated macrophages, and has been shown to be secreted from alveolar macrophages from smokers [Shapiro et al, 1993, Journal of Biological Chemistry, 268: 23824] as well as in foam cells in atherosclerotic lesions [Matsumoto et al, 1998, Am. J. Pathol. 153: 109]. A mouse model of COPD is based on challenge of mice with cigarette smoke for six months, two cigarettes a day six days a week. Wild-type mice developed pulmonary emphysema after this treatment. When MMP12 knock-out mice were tested in this model they developed no significant emphysema, strongly indicating that MMP12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29-38. It was recently discovered that smoking increases macrophage infiltration and macrophage-derived MMP-12 expression in human carotid artery plaques Kangavari [Matetzky S, Fishbein M C et al., Circulation 102:(18, 36-39 Suppl. S, Oct. 31, 2000].

MMP9 (Gelatinase B; 92 kDa TypeIV Collagenase; 92 kDa Gelatinase) is a secreted protein which was first purified, then cloned and sequenced, in 1989 [S. M. Wilhelm et al (1989) J. Biol. Chem. 264 (29): 17213-17221; published erratum in J. Biol. Chem. (1990) 265 (36): 22570]. A recent review of MMP9 provides an excellent source for detailed information and references on this protease: T. H. Vu & Z. Werb (1998) (In: Matrix Metalloproteinases, 1998, edited by W. C. Parks & R. P. Mecham, pp. 115-148, Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, the expression can be induced in these same cells and in other cell types by several mediators, including exposure of the cells to growth factors or cytokines. These are the same mediators often implicated in initiating an inflammatory response. As with other secreted MMPs, MMP9 is released as an inactive Pro-enzyme which is subsequently cleaved to form the enzymatically active enzyme. The proteases required for this activation in vivo are not known. The balance of active MMP9 versus inactive enzyme is further regulated in vivo by interaction with is TIMP-1 (Tissue Inhibitor of Metalloproteinases-1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues.

MMP9 release, measured using enzyme immunoassay, was significantly enhanced in fluids and in AM supernantants from untreated asthmatics compared with those from other populations [Am. J. Resp. Cell & Mol. Biol., November 1997, 17 (5):583-591]. Also, increased MMP9 expression has been observed in certain other pathological conditions, thereby implicating MMP9 in disease processes such as COPD, arthritis, tumour metastasis, Alzheimer's disease, multiple sclerosis, and plaque rupture in atherosclerosis leading to acute coronary conditions such as myocardial infarction.

A number of metalloproteinase inhibitors are known (see, for example, the reviews of MMP inhibitors by Beckett R. P. and Whittaker M., 1998, Exp. Opin. Ther. Patents, 8(3):259-282; and by Whittaker M. et al, 1999, Chemical Reviews 99(9):2735-2776).

WO 02/074767 discloses hydantoin derivatives of formula

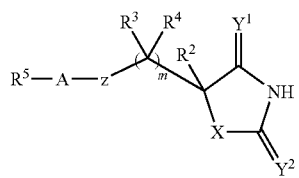

that are useful as MMP inhibitors, particularly as potent MMP12 inhibitors.

We now disclose a further group of hydantoin derivatives that are inhibitors of metalloproteinases and are of particular interest in inhibiting MMPs such as MMP12 and MMP9. The compounds of the present invention have beneficial potency, selectivity and/or pharmacokinetic properties.

In accordance with the present invention, there are provided compounds of formula (I)

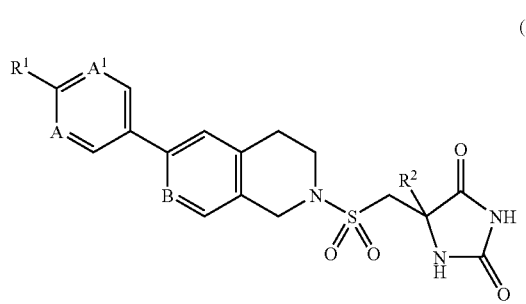

(I)

wherein $R^1$ represents cyclobutyl or cyclopropyl; said cyclopropyl group being optionally further substituted by $CH_3$, CN or one or two fluoro atoms;

$R^2$ represents C1 to 3 alkyl or cyclopropyl; and

A, $A^1$ and B independently represent CH or N;

and pharmaceutically acceptable salts thereof.

The compounds of formula (I) may exist in enantiomeric forms. It is to be understood that all enantiomers, diastereomers, racemates and mixtures thereof are included within the scope of the invention.

Compounds of formula (I) may also exist in various tautomeric forms. All possible tautomeric forms and mixtures thereof are included within the scope of the invention.

In one embodiment, $R^1$ represents cyclopropyl; said cyclopropyl group being optionally further substituted by one or two fluoro atoms.

In one embodiment, $R^1$ represents cyclopropyl.

In one embodiment, $R^2$ represents methyl or ethyl. In one embodiment, $R^2$ represents methyl.

In one embodiment, A and $A^1$ each represent N. In another embodiment, A represents N and $A^1$ represents-CH.

In one embodiment, B represents N. In another embodiment, B represents CH.

In one embodiment, $R^1$ represents cyclopropyl; $R^2$ represents methyl or ethyl; A and $A^1$ each represent N; and B represents CH.

In one embodiment, $R^1$ represents cyclopropyl; $R^2$ represents methyl or ethyl; A and $A^1$ each represent N; and B represents N.

In one embodiment, $R^1$ represents cyclopropyl; $R^2$ represents methyl or ethyl; A represents N and $A^1$ represents CH; and B represents N.

In one embodiment, $R^1$ represents cyclopropyl; $R^2$ represents methyl or ethyl; A represents N and $A^1$ represents CH; and B represents CH.

In one embodiment, $R^1$ represents cyclopropyl; said cyclopropyl group being optionally is further substituted by $CH_3$, CN or one or two fluoro atoms; $R^2$ represents C1 to 3 alkyl; and A, $A^1$ and B independently represent CH or N.

Unless otherwise indicated, the term "C1 to 3 alkyl" referred to herein denotes a straight or branched chain alkyl group having from 1 to 3 carbon atoms. Examples of such groups include methyl, ethyl, n-propyl and i-propyl.

Examples of a cyclopropyl ring optionally further substituted by one or two fluoro atoms include 1-fluoro-1-cyclopropyl, 2,2-difluoro-1-cyclopropyl and 2,3-difluoro-1-cyclopropyl:

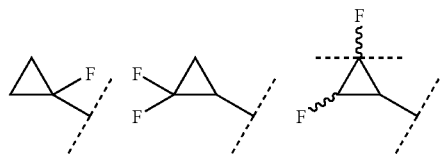

Examples of compounds of the invention include:
(5S)-5-({[6-(2-cyclopropylpyrimidin-5-yl)-3,4-dihydroisoquinolin-2(1H)-yl]sulfonyl}methyl)-5-methylimidazolidine-2,4-dione;
(5S)-5-({[6-(6-cyclopropylpyridin-3-yl)-3,4-dihydro-2,7-naphthyridin-2(1H)-yl]sulfonyl}methyl)-5-methylimidazolidine-2,4-dione;
(5S)-5-({[6-(2-cyclopropylpyrimidin-5-yl)-3,4-dihydro-2,7-naphthyridin-2(1H)-yl]sulfonyl}methyl)-5-methylimidazolidine-2,4-dione;
(5S)-5-({[6-(2-cyclopropylpyrimidin-5-yl)-3,4-dihydro-2,7-naphthyridin-2(1H)-yl]sulfonyl}methyl)-5-ethylimidazolidine-2,4-dione;
(5S)-5-({[6-(2-cyclopropylpyrimidin-5-yl)-3,4-dihydroisoquinolin-2(1H)-yl]sulfonyl}methyl)-5-ethylimidazolidine-2,4-dione;
(5S)-5-({[6-(2-cyclobutylpyrimidin-5-yl)-3,4-dihydroisoquinolin-2(1H)-yl]sulfonyl}methyl)-5-methylimidazolidine-2,4-dione;
(5S)-5-methyl-5-({[6-[2-(1-methylcyclopropyl)pyrimidin-5-yl]-3,4-dihydroisoquinolin-2(1H)-yl]sulfonyl}methyl) imidazolidine-2,4-dione;
(5S)-5-Cyclopropyl-5-({[6-(2-cyclopropylpyrimidin-5-yl)-3,4-dihydroisoquinolin-2(1H)-yl]sulfonyl}methyl)imidazolidine-2,4-dione;

and pharmaceutically acceptable salts thereof.

Each exemplified compound represents a particular and independent aspect of the invention.

The compounds of formula (I) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively the optical isomers may be obtained by asymmetric synthesis, or by synthesis from optically active starting materials.

Where optically isomers exist in the compounds of the invention, we disclose all individual optically active forms and combinations of these as individual specific embodiments of the invention, as well as their corresponding racemates.

Preferably the compounds of formula (I) have (5S)-stereochemistry as shown below:

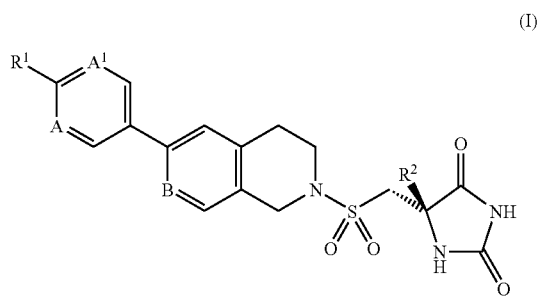

(I)

Where tautomers exist in the compounds of the invention, we disclose all individual tautomeric forms and combinations of these as individual specific embodiments of the invention.

The present invention includes compounds of formula (I) in the form of salts. Suitable salts include those formed with organic or inorganic acids or organic or inorganic bases. Such is salts will normally be pharmaceutically acceptable salts although non-pharmaceutically acceptable salts may be of utility in the preparation and purification of particular compounds. Such salts include acid addition salts such as hydrochloride, hydrobromide, citrate, tosylate and maleate salts and salts formed with phosphoric acid or sulphuric acid.

In another aspect suitable salts are base salts such as an alkali metal salt, for example, sodium or potassium, an alkaline earth metal salt, for example, calcium or magnesium, or an organic amine salt, for example, triethylamine.

Salts of compounds of formula (I) may be formed by reacting the free base or another salt thereof with one or more equivalents of an appropriate acid or base.

The compounds of formula (I) are useful because they possess pharmacological activity in animals and are thus potentially useful as pharmaceuticals. In particular, the compounds of the invention are metalloproteinase inhibitors and may thus be used in the treatment of diseases or conditions mediated by MMP12 and/or MMP9 such as asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and multiple sclerosis (MS), and haematological disorders.

In general, the compounds of the present invention are potent inhibitors of MMP9 and MMP12. The compounds of the present invention also show good selectivity with respect to a relative lack of inhibition of various other MMPs such as MMP8, MMP14 and MMP19.

Accordingly, the present invention provides a compound of formula (I), or a pharmaceutically acceptable salt thereof, as hereinbefore defined for use in therapy.

In another aspect, the invention provides the use of a compound of formula (I), or a pharmaceutically acceptable salt thereof, as hereinbefore defined in the manufacture of a medicament for use in therapy.

In another aspect, the invention provides the use of a compound of formula (I), or a pharmaceutically acceptable salt thereof, as hereinbefore defined in the manufacture of a medicament for use in the treatment of diseases or conditions in which inhibition of MMP12 and/or MMP9 is beneficial.

In another aspect, the invention provides the use of a compound of formula (I), or a pharmaceutically acceptable salt thereof, as hereinbefore defined in the manufacture of a medicament for use in the treatment of inflammatory disease.

In another aspect, the invention provides the use of a compound of formula (I), or a pharmaceutically acceptable salt thereof, as hereinbefore defined in the manufacture of a medicament for use in the treatment of an obstructive airways disease such as asthma or COPD.

In another aspect, the invention provides the use of a compound of formula (I), or a pharmaceutically acceptable salt thereof, as hereinbefore defined in the manufacture of a medicament for use in the treatment of rheumatoid arthritis, osteoarthritis, atherosclerosis, cancer or multiple sclerosis.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of treating a disease or condition in which inhibition of MMP12 and/or MMP9 is beneficial which comprises administering to a patient a therapeutically effective amount of a compound of formula (I) or a pharmaceutically acceptable salt thereof as hereinbefore defined.

The invention also provides a method of treating an obstructive airways disease, for example, asthma or COPD, which comprises administering to a patient a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder to be treated. The daily dosage of the compound of formula (I)/salt (active ingredient) may be in the range from 0.001 mg/kg to 75 mg/kg, in particular from 0.5 mg/kg to 30 mg/kg. This daily dose may be given in divided doses as necessary. Typically unit dosage forms will contain about 1 mg to 500 mg of a compound of this invention.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition. Conventional procedures for the selection and preparation of suitable pharmaceutical formulations are described in, for example, "Pharmaceuticals—The Science of Dosage Form Designs", M. E. Aulton, Churchill Livingstone, 1988.

Thus, the present invention also provides a pharmaceutical composition comprising a compound of formula (I) or a pharmaceutically acceptable salt thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions of this invention may be administered in a standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more diseases or conditions referred to hereinabove such as "Symbicort" (trade mark) product.

The present invention further provides a process for the preparation of a compound of formula (I) or a pharmaceutically acceptable salt thereof as defined above which, comprises:

a) reaction of a compound of formula (II)

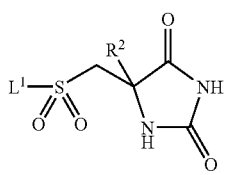

(II)

wherein $R^2$ is as defined in formula (I) and $L^1$ represents a leaving group, with a compound of formula (III) (or a salt thereof)

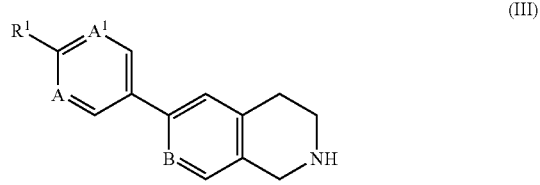

(III)

wherein $R^1$, A, $A^1$ and B are as defined in formula (I); or b) reaction of a compound of formula (V)

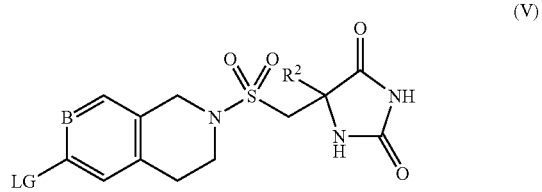

(V)

wherein $R^2$ and B are as defined in formula (I) and LG is a leaving group; with a boronic acid derivative of formula (XII)

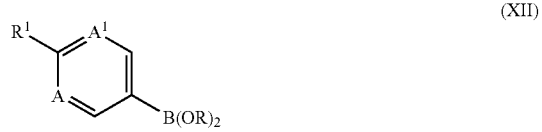

(XII)

wherein $R^1$, A and $A^1$ are as defined in formula (I); or c) reaction of a compound of formula (IX)

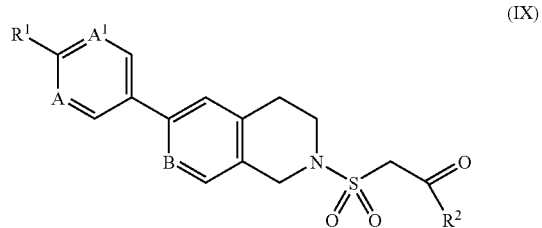

(IX)

wherein $R^1$, $R^2$, A, $A^1$ and B are as defined in formula (I); with ammonium carbonate and potassium cyanide;

and optionally thereafter forming a pharmaceutically acceptable salt thereof.

In the above process (a), suitable leaving groups $L^1$ include halo, particularly chloro or trifluoromethylsulfonate. The reaction is preferably performed in a suitable solvent optionally in the presence of an added base for a suitable period of time, typically 0.5 to 16 h, at ambient to reflux temperature. Typically solvents such as N,N-dimethylformamide, pyridine, tetrahydrofuran, acetonitrile, N-methylpyrrolidine or dichloromethane are used. When used, the added base may be an organic base such as triethylamine, N,N-diisopropylethylamine, N-methylmorpholine or pyridine, or an inorganic base such as an alkali metal carbonate. The reaction is typically conducted at ambient temperature for 0.5 to 16 h, or until completion of the reaction has been achieved, as determined by chromatographic or spectroscopic methods. Reactions of sulfonyl halides with various primary and secondary amines are well known in the literature, and the variations of the conditions will be evident for those skilled in the art.

Sulfonylchlorides of formula (II) wherein $L^1$ represents chloro and $R^2$ represents Me are disclosed in WO 02/074767 and references cited therein. Corresponding compounds wherein $R^2$ represents C1 to 3 alkyl may be prepared using analogous methods.

Suitable processes for the preparation of compounds of formula (I) are described in a retrosynthetic way in Scheme 1.

electrophile (XI) and a boron reagent (VIIIa-c). The latter can be obtained from (VIIa-c) using standard Miyaura conditions (*J. Org. Chem.* 1995, 60, 7508-7510). Deprotection of (IVa-c) either by hydrogen chloride in methanol (PG=tert-butoxycarbonyl) or refluxing 1-chloroethyl chloroformate/refluxing methanol (PG=tert-butyl or benzyl) (*Synlett*. 1993, 195-196) gives amine (IIIa-c) as a hydrochloride salt. The free base can be obtained by treatment of (IIIa-c) with base and extraction with an organic solvent such as ethyl acetate is or toluene. Reacting (IIIa-c) either as a salt or base in a suitable solvent (e.g. acetonitrile, tetrahydrofuran, N-methylpyrrolidine or N,N-dimethylformamide) with the sulfonyl chloride (II) in

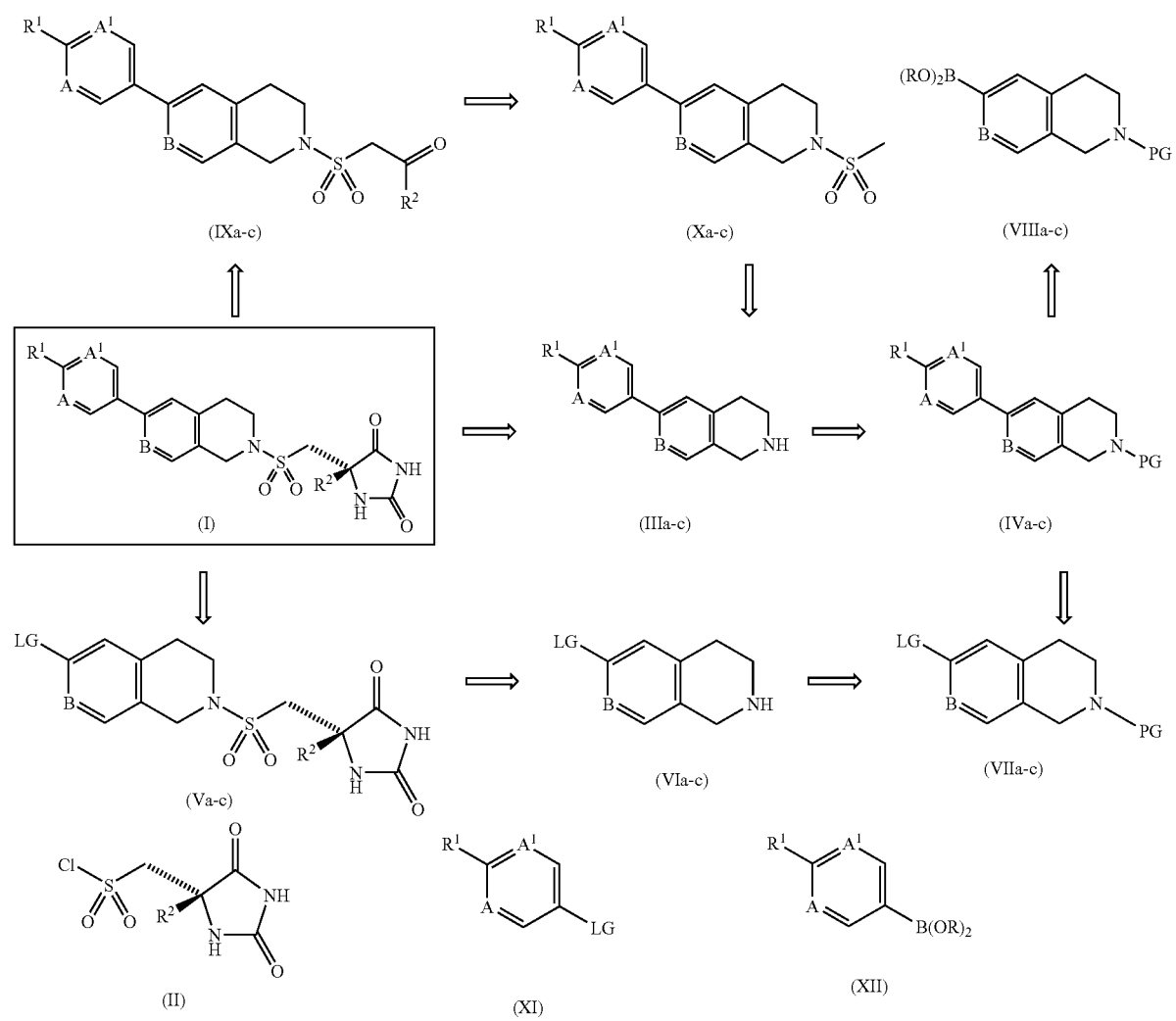

Scheme 1

In Scheme 1, protecting groups (PG) can be either carbamates (e.g. tert-butoxycarbamate), amides (e.g. trifluoroacetyl) or alkyl (e.g. tert-butyl or benzyl). Leaving groups (LG) can be either chloride, bromide, iodide or trifluoromethylsulfonate. In the palladium-catalysed Suzuki couplings, either boronic acids or pinacolboronates may be used. Intermediate (IVa-c) can be prepared by standard Suzuki coupling (*Chem. Rev.* 1995, 95, 2457) between an electrophile (VIIa-c) and a boron reagent (XII), or the other way around, between an the presence of a tertiary amine (e.g. triethylamine, pyridine or N,N-diisopropylethylamine) for 0.5 to 16 hours produces compounds of formula (I).

An alternative route to compounds of formula (I) from intermediate (IIIa-c) via methanesulfonamide (Xa-c) and ketone (IXa-c) has been previously described (WO 02/074767). Briefly, treatment of (IIIa-c) with methansulfonyl chloride and a tertiary amine (e.g. triethylamine, pyridine or N,N-diisopropylethylamine) in a suitable solvent (e.g.

dichloromethane or tetrahydrofuran) produces the methansulfonamide (Xa-c) which in turn can be transformed into the ketone (IXa-c) using standard procedures. Heating ketone (IXa-c) with ammonium carbonate and potassium cyanide in 50% aqueous ethanol in a sealed vial at 80-90° C. for 1 to 5 hours gives a racemic hydantoin that can be resolved by chiral chromatography (e.g. on OD-H with 100% ethanol).

In a third route, intermediate (VIIa-c) is deprotected as described above to give amine (VIa-c) as a hydrochloride salt. The free base can be isolated by treatment with base and extraction with an organic solvent e.g. ethyl acetate or toluene. Reacting (VIa-c) either as a salt or base in a suitable solvent (e.g. acetonitrile, tetrahydrofuran, N-methylpyrrolidine or N,N-dimethylformamide) with sulfonyl chloride (II) in the presence of a tertiary amine (e.g. triethylamine, pyridine or N,N-diisopropylethylamine) for 0.5 to 16 hours produces chiral sulfonamide (Va-c). The latter can be coupled with boron reagent (XII) using standard Suzuki conditions to give compounds of formula (I).

Intermediates (VIIa-b) are conveniently prepared using the following methods.

The 1,2,3,4-tetrahydroisoquinoline Intermediate (VIIa)

Methods for the synthesis of 1,2,3,4-tetrahydroisoquinolines are well known in the literature. The classical route is the Pomeranz-Fritz reaction of benzaldehydes with a diacetal protected aminoacetaldehyde (*Org. React.* 1951, 6, 191) yielding the isoquinoline nucleus which upon catalytical reduction gives 1,2,3,4-tetrahydro-isoquinolines. Another route is the Bischler-Napieralski reaction (*Org. React.* 1951, 6, 74) of a carbamate of 2-phenylethanamines with phosphoryl chloride in refluxing toluene or xylenes. Reduction of the resulting cyclic benzamide with lithium aluminium hydride in tetrahydrofuran (*J. Med. Chem.* 1987, 30(12), 2208-2216) or diborane in tetrahydrofuran (*J. Med. Chem.* 1980, 23(5), 506-511) affords the 1,2,3,4-tetrahydroisoquinoline. A variation of the Bischler-Napieralski reaction is the Pictet-Spengler synthesis (*Org. React.* 1951, 6, 151). In this reaction amides, carbamates or sulfonamides of 2-phenylethanamines are heated with paraformaldehyde and strong proton acids (e.g. trifluoroacetic acid, sulfuric acid) or Lewis acids in a solvent (e.g. dichloromethane, toluene, formic acid) to give the 1,2,3,4-tetrahydroisoquinoline in a single step (*Tetrahedron* 2002, 58(8), 1471-1478).

Scheme 2

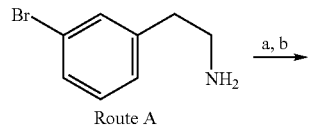

Route A

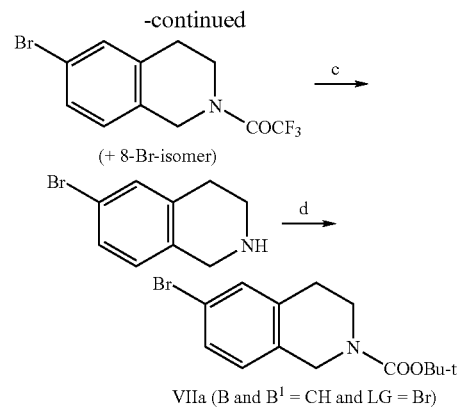

Reagents:
a (CF$_3$CO)$_2$O, Et$_3$N; +4° C.
b (HCHO)$_n$, H$_2$SO$_4$, HOAc; RT.
c NaBH$_4$, EtOH; RT or NH$_3$ (conc), EtOH, heat.
d (t-BuOCO)$_2$O, Et$_3$N, DCM, RT.

Preferably the 1,2,3,4-tetrahydroisoquinoline intermediate (VIIa) is synthesised by Route A shown in Scheme 2. This route is a Friedel-Craft-type reaction of N-[2-(3-bromophenyl)ethyl]-2,2,2-trifluoroacetamide with formaldehyde and sulfuric acid in acetic acid (*Tetrahedron Lett.* 1996, 37(31), 5453-5456) giving a mixture of the 6-bromo- and 8-bromoisomer in a ratio of 3 to 1. Replacement of the trifluoroacetamide group with a BOC-group gives (VIIa). The regioisomers are not conveniently separated at this stage.

The 1,2,3,4-tetrahydro-2,7-naphthyridine Intermediate (VIIB)

In contrast to the 1,2,3,4-tetrahydroisoquinolines, there are rather few examples of synthetic methods for 1,2,3,4-tetrahydro-2,7-naphthyridines in the literature. One important method to prepare 1,2,3,4-tetrahydro-2,7-naphthyridine is the regio-selective catalytic reduction of 2,7-naphthyridine (*Eur. J. Med. Chem. Ther.* 1996, 31(11), 875-888). The synthesis of 2,7-naphthyridine and some derivatives thereof has been described in the literature. One classical route involves several steps and starts with the acid catalysed condensation of malononitrile with diethyl 1,3-acetonedicarboxylate (*J. Chem. Soc.* 1960, 3513-3515; see also *J. Heterocycl. Chem.* 1970, 7, 419-421). A slightly different route to 2,7-naphthyridine involves oxidation of 4-formyl-2,7-naphthyridine to give 2,7-naphthyridine-4-carboxylic acid followed by decarboxylation (Synthesis 1973, 46-47). A completely different method is based on the internal Diels-Alder reaction of N-(ethoxycarbonyl)-N-(but-3-ynyl)amino-methylpyrazine and gives a mixture of 1,2,3,4-tetrahydro-2,7-naphthyridine and 5,6,7,8-tetrahydro-1,7-naphthyridine after hydrolysis of the carbamate group (WO 02/064574).

Scheme 3

Route B

MeO—[pyridine]—CHO →(a,b)→ MeO—[pyridine-I]—CHO →(c)→ MeO—[pyridine-C≡C-SiMe$_3$]—CHO →(d)→ MeO—[2,7-naphthyridine]

↓ e

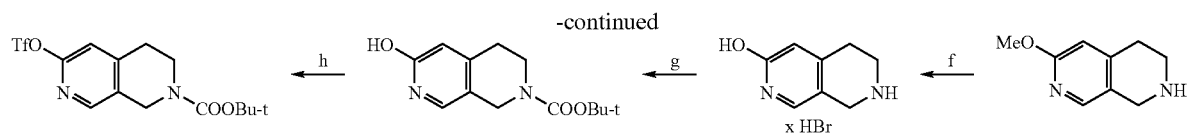

Reagents:
a LiCH₃NCH₂CH₂N(CH₃)₂, THF, -70° C.,
b n-BuLi in hexanes, -70° C., then I₂.
c TMS-acetylene, PdCl₂(PPh₃)₂, CuI, Et₃N, THF, 60° C.
d 7M NH₃, EtOH, 80° C.
e H₂, PtO₂, HOAc.
f 48% HBr (aq), 120° C.
g (BOC)O, Et₃N, H₂O, THF.
h Tf₂O, PhMe, 30% K₃PO₄.

Preferably the 1,2,3,4-tetrahydro-2,7-naphthyridine intermediate (VIIb) can be synthesised as shown in Schemes 3 and 4. In Route B, commercially available 6-methoxynicotinaldehyde is treated successively with the lithium salt of N,N,N'-trimethylethylenediamine, then n-BuLi in hexanes and finally iodine to afford the 4-iodo-6-methoxynicotinaldehyde (cf. *Tetrahedron Lett.* 1993, 34(39), 6173-6176). The iodo compound is coupled with trimethylsilylacetylene under usual Sonagashira-Hagihara conditions (*Synthesis* 1980, 627-630) and the resulting 6-methoxy-4-[(trimethylsilyl) ethynyl]nicotinaldehyde is condensed with ammonium hydroxide in ethanol to give 3-methoxy-2,7-naphthyridine (*Synthesis* 1999, 2, 306-311). Regioselective catalytical reduction (cf. *Eur. J. Med. Chem. Ther.* 1996, 31(11), 875-888) affords 6-methoxy-1,2,3,4-tetrahydro-2,7-naphthyridine. Demethylation and N-protection with BOC-anhydride and finally treatment of the resulting tert-butyl 6-hydroxy-3,4-dihydro-2,7-naphthyridine-2(1H)-carboxylate with triflic anhydride in a two-phase system gives (VIIb).

dride in methanol to give 2-tert-butyl-6-methoxy-1,2,3,4-tetrahydro-2,7-naphthyridine. Cleavage of the methyl group with refluxing 48% hydrobromic acid and treatment with triflic anhydride in the presence of base gives (VIIb) protected as the tert-butylamine.

It will be appreciated by those skilled in the art that in the processes of the present invention certain potentially reactive functional groups such as hydroxyl or amino groups in the starting reagents or intermediate compounds may need to be protected by suitable protecting groups. Thus, the preparation of the compounds of the invention may involve, at various stages, the addition and removal of one or more protecting groups.

Suitable protecting groups and details of processes for adding and removing such groups are described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley-Interscience (1999).

Scheme 4

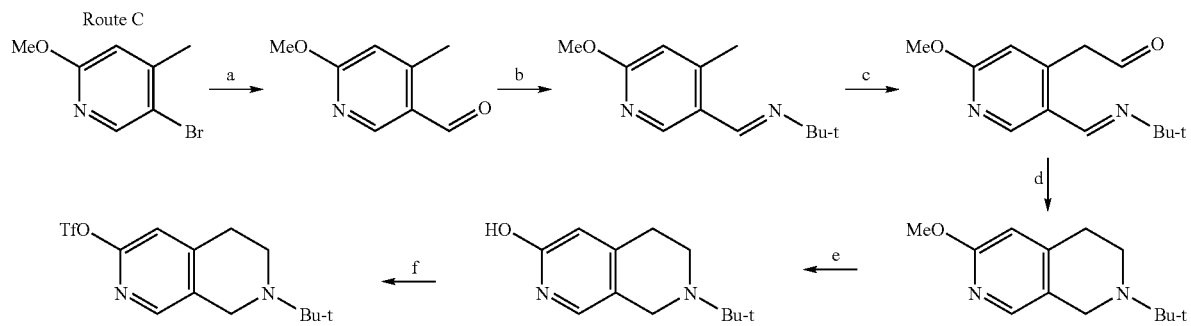

Reagents;
a n-BuLi, THF, -70° C. then DMF, -70° C. to RT.
b t-BuNH₂, DCM, 3Å mol. sieves.
c Li-TMP, -20° C. then DMF, -20 to -10° C.
d NaBH₃CN, MeOH, HOAc; RT.
e 48% HBr (aq), reflux; work-up with K₂CO₃ (aq).
f Tf₂O, pyridine +4° C.

In Route C, commercially available 5-bromo-2-methoxy-4-methylpyridine in anhydrous tetrahydrofuran is metallated with n-BuLi and then treated with N,N-dimethylformamide to afford 6-methoxy-4-methylnicotinaldehyde. This was converted to the tert-butylimine with tert-butylamine in dichloromethane. Metallation with lithium 2,2,6,6-tetramethylpiperidide (Li-TMP) (cf. *J. Org. Chem.* 1993, 58, 2463-2467) and addition of N,N-dimethylformamide affords the iminoacetaldehyde which is reduced with sodium cyanoborohy- The compounds of the invention and intermediates thereto may be isolated from their reaction mixtures and, if necessary further purified, by using standard techniques.

The present invention will now be further explained by reference to the following illustrative examples.

General Methods

¹H NMR and ¹³C NMR spectra were recorded on a Varian Inova 400 MHz or a Varian Mercury-VX 300 MHz instrument. The central peaks of chloroform-d ($\delta_H$ 7.27 ppm), dimethylsulfoxide-$d_6$ ($\delta_H$ 2.50 ppm), acetonitrile-$d_3$ ($\delta_H$ 1.95 ppm) or methanol-$d_4$ ($\delta_H$ 3.31 ppm) were used as internal references. Column chromatography was carried out using silica gel (0.040-0.063 mm, Merck) with a slight over-pressure (0.2-0.4 bars) applied on the column. A Kromasil KR-100-5-$C_{18}$ column (250×20 mm, Akzo Nobel) and mixtures of acetonitrile/water with 0.1% TFA at a flow rate of 10 mL/min were used for preparative HPLC. Unless stated otherwise, starting materials were commercially available. All solvents and commercial reagents were of laboratory grade and were used as received. The organic phases from extractions were dried over anhydrous sodium sulfate if not stated otherwise. Organic phases or solutions were concentrated by rotary evaporation. Yields were not optimised.

The Following Method was Used for LC-MS Analysis:

Instrument Agilent 1100; Column Waters Symmetry 2.1× 30 mm; Mass APCI; Flow rate 0.7 mL/min; Wavelength 254 or 220 nm; Solvent A: water+0.1% TFA; Solvent B: acetonitrile+0.1% TFA; Gradient 15-95%/B 2.7 min, 95% B 0.3 min.

The Following Method was Used for GC-MS Analysis:

Instrument Hewlett Packard 5890 Series II; Column Agilent HP-5 (30 m×0.32 mm ID); Mass selective detector Hewlett Packard 5971 Series; Pressure 55 kPa He; Oven program 100° C. (3 min) to 300° C., 25° C./min.

| Abbreviations: | |
|---|---|
| BOC-anhydride | di-tert-butyl dicarbonate |
| n-BuLi | n-butyl lithium |
| DCM | dichloromethane |
| DIPEA | N,N-diisopropylethylamine |
| DMF | N,N-dimethylformamide |
| DMSO | dimethylsulfoxide |
| EtOAc | ethyl acetate |
| EtOH | ethanol |
| GC-MS | gas chromatography-mass spectrometry |
| LDA | lithium diisopropylamide |
| MeOH | methanol |
| LC-MS | liquid chromatography-mass spectroscopy |
| $PdCl_2 \times dppf$ | 1,1'-bis(diphenylphosphino)ferrocene palladium(II)dichloride |
| RT | room temperature, normally 20 to 22° C. |
| TEA | triethylamine |
| THF | tetrahydrofuran |
| TBME | tert-butyl methyl ether |
| TFA | trifluoroacetic acid |
| Triflic anhydride | trifluoromethanesulfonic anhydride ($Tf_2O$) |

EXAMPLE 1

(5S)-5-({[6-(2-Cyclopropylpyrimidin-5-yl)-3,4-dihydroisoquinolin-2(1H)-yl]sulfonyl}methyl)-5-methylimidazolidine-2,4-dione

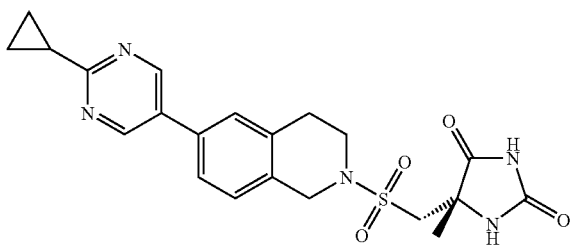

[(4S)-4-Methyl-2,5-dioxoimidazolidin-4-yl]methanesulfonyl chloride (0.020 g, 0.087 mmol) in anhydrous THF (0.40 mL) was added dropwise to a stirred solution of 6-[2-(cyclopropyl)pyrimidin-5-yl]-1,2,3,4-tetrahydroisoquinoline (0.023 g, 0.091 mmol), DIPEA (0.022 mL, 0.13 mmol) and dry THF (0.50 mL) at RT. After the addition was complete, the solution was stirred at RT for 2 h and then taken up in water-brine and extracted twice with EtOAc. The combined organic phases were washed with brine, dried, filtered and concentrated to give a crude product. Purification by preparative HPLC afforded 0.021 g (50%) of the title compound as a white solid.

LC-MS m/z 442 (M+1);

$^1$H NMR ($CD_3CN$) δ 8.97 (s, 2H), 8.62 (br s, 1H), 7.52 (s, 1H), 7.51 (dd, 1H), 7.30 (d, 1H), 6.40 (br s, 1H), 4.48 (s, 2H), 3.54 (t, 2H), 3.51 (d, 1H), 3.42 (d, 1H), 3.01 (t, 2H), 2.38 (m, 1H), 1.48 (s, 3H) and 1.23 (m, 4H) ppm.

The starting materials were prepared as follows:

6-[2-(Cyclopropyl)pyrimidin-5-yl]-1,2,3,4-tetrahydroisoquinoline tert-Butyl 6-[2-(cyclopropyl)pyrimidin-5-yl]-3,4-dihydroisoquinoline-2(1H)-carboxylate (0.034 g, 0.13 mmol) was stirred in TFA (1.0 mL) and DCM (1.0 mL) at RT overnight, then concentrated twice, the second time with added toluene (5 mL), to afford the trifluoroacetate of the title product.

$^1$H NMR ($CD_3OD$) δ 8.87 (s, 2H), 7.60 (d, 1H), 7.59 (s, 1H), 7.37 (d, 1H), 4.43 (s, 2H), 3.55 (t, 2H), 3.21 (t, 2H), 2.27 (m, 1H), and 1.14 (m, 4H) ppm.

The crude product was taken up in 1M sodium carbonate solution (10 mL) and extracted twice with EtOAc. The combined organic phases were washed with brine, dried, filtered and concentrated to give 0.023 g (94%) of the title product as a white solid.

LC-MS m/z 252 (M+1).

5-Bromo-2-cyclopropylpyrimidine

The title compound was prepared according to Hickey et al. (WO 00/066566).

LC-MS m/z 199/201 (M+1);

$^1$H NMR ($CDCl_3$) δ 8.61 (s, 2H), 2.30-2.18 (m, 1H) and 1.15-1.10 (m, 4H) ppm.

tert-Butyl 6-[2-(cyclopropyl)pyrimidin-5-yl]-3,4-dihydroisoquinoline-2(1H)-carboxylate A 4:1 mixture (0.097 g, 0.27 mmol) of tert-butyl 6-(4,4,5,5-tetramethyl-1,3,2-dioxaborolan-2-yl)-3,4-dihydroisoquinoline-2(1H)-carboxylate and tert-butyl 8-(4,4,5,5-tetramethyl-1,3,2-dioxaborolan-2-yl)-3,4-dihydroisoquinoline-2(1H)-carboxylate, 5-bromo-2-cyclopropylpyrimidine (0.054 g, 0.27 mmol), $PdCl_2 \times dppf$ (0.0045 g), 2M sodium carbonate (1.0 mL), toluene (4.0 mL) and EtOH (1.0 mL) was purged with dry argon for ten minutes, then heated in a sealed vial at 81° C. for 6 h. The black solution was filtered through glass-wool, taken up in water-brine and washed twice with EtOAc. The combined organic phases were dried, filtered and concentrated with silica (5 g). Column chromatography with EtOAc-heptanes (1:5 through 1:2) gave 0.034 g (36%) of the title product as white solid.

LC-MS m/z 352 (M+1);

$^1$H NMR ($CDCl_3$) δ 8.74 (s, 2H), 7.35 (dd, 1H), 7.29 (s, 1H), 7.22 (d, 1H), 4.62 (s, 2H), 3.68 (t, 2H), 2.90 (t, 2H), 2.30 (m, 1H), 1.50 (s, 9H), 1.18 (m, 2H) and 1.11 (m, 2H) ppm.

tert-Butyl 6-(4,4,5,5-tetramethyl-1,3,2-dioxaborolan-2-yl)-3,4-dihydroisoquinoline-2(1H)-carboxylate A 3:1 mixture (0.49 g, 1.6 mmol) of tert-butyl 6-bromo-3,4-dihydroisoquinoline-2(1H)-carboxylate and tert-butyl 8-bromo-3,4-dihydroisoquinoline-2(1H)-carboxylate, bis(pinacolato)diborane (0.45 g, 1.8 mmol), PdCl$_2$×dppf (0.039 g, 0.048 mmol), potassium acetate (0.48 g, 4.8 mmol) and DMF (8.0 mL) was heated at 81° C. overnight. The solvent was evaporate, the residue taken up in water-brine and washed twice with EtOAc. The organic phase was dried, filtered and concentrated. Column chromatography with EtOAc-heptanes (1:10 through 1:4) gave 0.24 g of a 4:1 mixture of the title product and tert-butyl 8-(4,4,5,5-tetramethyl-1,3,2-dioxaborolan-2-yl)-3,4-dihydroisoquinoline-2(1H)-carboxylate.

$^1$H NMR (CDCl$_3$) δ 7.62 (d, 1H), 7.60 (s, 1H), 7.13 (d, 1H), 4.59 (s, 2H), 3.64 (t, 2H), 2.85 (t, 2H), 1.50 (s, 9H) and 1.35 (s, 12H) ppm (6-isomer).

$^1$H NMR (CDCl$_3$) δ 7.69 (d, 1H), 7.24-7.14 (m's, 2H), 4.88 (s, 2H), 3.64 (t, 2H), 2.85 (t, 2H), 1.50 (s, 9H) and 1.35 (s, 12H) ppm (8-isomer).

tert-Butyl 6-bromo-3,4-dihydroisoquinoline-2(1H)-carboxylate

6-Bromo-2-(trifluoroacetyl)-1,2,3,4-tetrahydroisoquinoline was prepared in two steps from [2-(3-bromophenyl)ethyl]amine (4.0 g, 20 mmol) following the procedure of Stokker (*Tetrahedron Lett.* 1996, 37(31), 5453-5456). Column chromatography with EtOAc-heptanes (1:10 through 1:6) gave 2.3 g (7.5 mmol) of a 3:1 mixture of 6-bromo-2-(trifluoroacetyl)-1,2,3,4-tetrahydroisoquinoline and 8-bromo-2-(trifluoroacetyl)-1,2,3,4-tetrahydroisoquinoline.

$^1$H NMR (CDCl$_3$) δ 7.62 (d, 1H), 7.60 (s, 1H), 7.13 (d, 1H), 4.59 (s, 2H), 3.64 (t, 2H), 2.85 (t, 2H) and 1.50 (s, 9H) and 1.35 (s, 12H) ppm (6-isomer).

$^1$H NMR (CDCl$_3$) δ 7.69 (d, 1H), 7.24-7.14 (m, 2H), 4.88 (s, 2H), 3.64 (t, 2H), 2.85 (t, 2H) and 1.50 (s, 9H) and 1.35 (s, 12H) ppm (8-isomer).

This mixture was stirred with absolute EtOH (100 mL) and 25% ammonium hydroxide (10 mL) at 60° C. for 4 h. More 25% ammonium hydroxide (15 mL) was added and stirring continued at RT overnight. The volatiles were evaporated to leave the crude amine as a white solid. LC-MS m/z 212/214 (M+1).

Dry THF (50 mL) and DIPEA (1.3 mL, 7.5 mmol) were added followed by BOC-anhydride (1.8 g, 8.2 mmol). The mixture was stirred overnight at RT. The volatiles were evaporated and the residue was taken up in water. The pH was adjusted to 2 with 1M phosphoric acid and the product was extracted twice with EtOAc. The combined organic phases were washed with brine made slightly alkaline with saturated sodium bicarbonate, dried, filtered and concentrated. The crude product was purified by column chromatography with EtOAc-heptanes (1:50 through 1:20) to give 2.24 g (96%) of a 3:1 mixture of the title product and tert-butyl 8-bromo-3,4-dihydroisoquinoline-2(1H)-carboxylate.

LC-MS m/Z 256/258 (M−56);

$^1$H NMR (CDCl$_3$) δ 7.31 (dd, 1H), 7.30 (br s, 1H), 6.98 (d, 1H), 4.52 (s, 2H), 3.63 (t, 2H), 2.81 (t, 2H) and 1.50 (s, 9H) ppm (6-isomer).

$^1$H NMR (CDCl$_3$) δ 7.42 (dd, 1H), 7.12-7.01 (m's, 2H), 4.55 (s, 2H), 3.64 (t, 2H), 2.84 (t, 2H) and 1.51 (s, 9H) ppm (8-isomer).

Alternatively, 6-(2-cyclopropyl-pyrimidin-5-yl)-1,2,3,4-tetrahydro-isoquinoline may be prepared as follows:

a) 1,2,3,4-Tetrahydro-isoquinolin-6-ol hydrobromide

6-Methoxy-1,2,3,4-tetrahydro-isoquinoline hydrochloride, prepared as in WO 2004/26305, (18.9 g, 94 mmol) in 48% aqueous hydrobromic acid was heated at 100° C. for 12 h and then cooled to 0° C. The solid was filtered off, washed with t-butyl methyl ether and dried.

Yield=17.1 g (79%)

APCI-MS m/z: 150 [M+H$^+$];

$^1$H NMR (400 MHz, DMSO-d$_6$) δ2.91 (t, 2H), 3.27-3.35 (m, 2H), 4.13 (t, 2H), 4.52 (s, 1H), 6.59 (d, 1H), 6.66 (dd, 1H), 7.00 (d, 1H), 9.07 (s, 2H) ppm.

b) 6-Trifluoromethanesulfonyloxy-3,4-dihydro-1H-isoquinoline-2-carboxylic acid tert-butyl ester

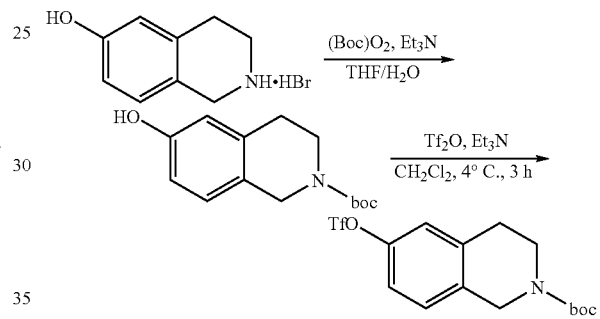

The above two steps were performed as described in Synthetic Communications, 25(20), 3255-3261, (1995).

c) 6-(2-Cyclopropyl-pyrimidin-5-yl)-3,4-dihydro-1H-isoquinoline-2-carboxylic acid tert-butyl ester 6-Trifluoromethanesulfonyloxy-3,4-dihydro-1H-isoquinoline-2-carboxylic acid tert-butyl ester (11.51 g, 30 mmol) was dissolved in DMF (250 mL) and the yellow solution was purged by bubbling argon (g) through the solution. Potassium acetate (8.83 g, 90 mmol), bis(pinacolato)diboron (8.38 g, 33 mmol), PdCl$_2$ dppf (1.22 g, 1.5 mmol) and dppf (0.83 g, 1.5 mmol) were added and the mixture was purged again with argon. The mixture was then heated to 90° C. for 2 h. Tripotassium phosphate monohydrate (18 g, 78 mmol) was added followed by 2-cyclopropyl-5-bromo-pyrimidine (7.76 g, 39 mmol) and stirring was continued for 5 h at 90° C. The reaction mixture was poured onto saturated sodium bicarbonate solution and extracted several times with ethyl acetate. The ethyl acetate solution was dried over magnesium sulphate, the drying agent filtered off and the filtrate was evaporated. The residue was purified by flash chromatography eluting with ethyl acetate:heptane (1:3) to give 8.1 g (76%) of the title compound as a colourless solid.

APCI-MS m/z: 352 [M+H$^+$];

$^1$H-NMR (CDCl$_3$): δ 8.77 (2H, s), 7.36 (1H, d), 7.31 (1H, brs), 7.24 (1H, d), 4.63 (2H, s), 3.70 (2H, brt), 2.92 (2H, brt), 2.35 (1H, m), 1.51 (9H, s), 1.24-1.10 (4H, m) ppm.

d) 6-(2-Cyclopropyl-pyrimidin-5-yl)-1,2,3,4-tetrahydro-isoquinoline 6-(2-Cyclopropyl-pyrimidin-5-yl)-3,4-dihydro-1H-isoquinoline-2-carboxylic acid tert-butyl ester (9.49 g, 27 mmol) was dissolved in ethyl acetate (100 mL) at 50° C., and to this warm solution was added 1.5M hydrogen chloride in ethyl acetate (200 mL). After 1 h, the mixture was cooled to room temperature and the solid was filtered off and dried.

APCI-MS m/z: 252 [M+H$^+$];

$^1$H-NMR (CD$_3$OD): δ 9.35 (2H, s), 7.76-7.70 (2H, brs+brdd), 7.46 (1H, d), 4.47 (2H, s), 3.57 (2H, t), 3.25 (2H, t), 2.46 (1H, m), 1.51-1.45 (4H, m) ppm.

$^{13}$C-NMR (CD$_3$OD): δ 168.39, 155.82, 134.34, 132.65, 132.52, 131.32, 129.22, 128.74, 126.69, 45.56, 42.69, 26.17, 16.51, 14.11 ppm.

The dihydrochloride salt (8.82 g, 27 mmol) was suspended in water (100 mL) and 2M NaOH (300 mL) was added. The mixture was then extracted with 4:1 ethyl acetate/diethyl ether (4×300 mL). The combined organic phases were dried over anhydrous potassium carbonate, filtered and evaporated to give the title compound as the free base (6.65 g).

APCI-MS m/z: 252 [M+H$^+$];

$^1$H-NMR (CD$_3$OD): δ 8.81 (2H, s), 7.43-7.38 (2H, d+s), 7.18 (1H, d), 3.99 (2H, s), 3.10 (2H, t), 2.90 (2H, t), 2.25 (1H, m), 1.18-1.06 (4H, m) ppm.

$^{13}$C-NMR (CD$_3$OD): δ 171.53, 155.83, 137.05, 137.01, 133.50, 132.32, 128.51, 128.36, 125.20, 48.35, 44.28, 29.49, 18.38, 11.16 ppm.

EXAMPLE 2

(5S)-5-({[6-(6-Cyclopropylpyridin-3-yl)-3,4-dihydro-2,7-naphthyridin-2(1H)-yl]sulfonyl}methyl)-5-methylimidazolidine-2,4-dione

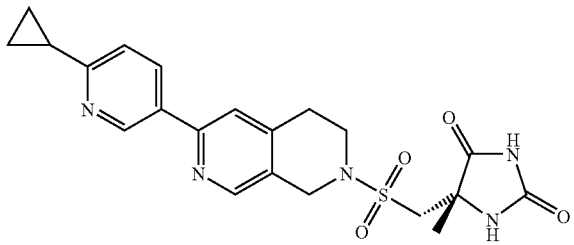

The title compound was prepared from 6-(6-cyclopropylpyridin-3-yl)-1,2,3,4-tetrahydro-2,7-naphthyridine hydrochloride (0.63 mmol) and [(4S)-4-methyl-2,5-dioxoimidazolidin-4-yl]methanesulfonyl chloride (0.70 mmol) following the general procedure of Example 1. Column chromatography with neat EtOAc and EtOAc-MeOH (9:1) as eluents gave 0.060 g of almost pure product. Recrystallisation from 99% EtOH gave 0.019 g (7.0%) of the title compound as white solid.

LC-MS m/z 442 (M+1);

$^1$H NMR (DMSO-d$_6$) δ 10.8 (s, 1H), 9.06 (d, 1H), 8.49 (s, 1H), 8.26 (dd, 1H), 8.06 (s, 1H), 7.83 (s, 1H), 7.39 (d, 1H), 4.45 (s, 2H), 3.61 (d, 1H), 3.48 (d, 1H), 3.46 (m, 2H), 2.97 (m, 2H), 2.16 (m, 1H), 1.34 (s, 3H) and 1.02-0.94 (m, 4H) ppm.

The starting materials were prepared as follows:

6-(6-Cyclopropylpyridin-3-yl)-1,2,3,4-tetrahydro-2,7-naphthridine hydrochloride tert-Butyl 6-{[(trifluoromethyl)sulfonyl]oxy}-3,4-dihydro-2,7-naphthyridine-2(1H)-carboxylate (0.34 g, 0.90 mmol), 2-cyclopropyl-5-(4,4,5,5-tetramethyl-1,3,2-dioxaborolan-2-yl)pyridine (0.20 g, 0.82 mmol), PdCl$_2$×dppf (0.050 g), saturated sodium carbonate (2 mL), EtOH (4 mL) and toluene (4 mL) were stirred at 80° C. for 2 h. The solution was cooled to RT, taken up in water (15 mL) and extracted three times with EtOAc-Et$_2$O. The combined organic phases were dried, filtered and concentrated. Purification by column chromatography with EtOAc-heptanes (1:1 through 3:1) and EtOAc-MeOH (9:1) as eluents gave 0.22 g (70%) of tert-butyl 6-(6-cyclopropylpyridin-3-yl)-3,4-dihydro-2,7-naphthyridine-2(1H)-carboxylate as a white solid.

LC-MS m/z 352 (M+1).

This material was dissolved in EtOAc (5 mL) and stirred with 1.5M hydrogen chloride in EtOAc (5 mL) at 50° C. for 4 h. The solvent was evaporated to leave the crude title compound (0.63 mmoles) in quantitative yield.

2-Cyclopropyl-5-(4,4,5,5-tetramethyl-1,3,2-dioxaborolan-2-yl)pyridine 0.5M Zinc chloride in THF (5.5 mL, 2.8 mmol) was added to a solution of 0.5M cyclopropylmagnesium bromide in THF (5.5 mL, 2.8 mmol) under argon. The solution was stirred at RT for 2 h at which time a slurry had formed. To this slurry was added in one portion 2,5-dibromopyridine (0.65 g, 2.8 mmol) and PdCl$_2$×dppf (0.041 g, 0.050 mmol). After a few minutes an exotherm was seen and the slurry became thicker, the exotherm subsided and the slurry was stirred at RT overnight. The reaction mixture was poured into saturated sodium bicarbonate solution and extracted with ether. The ether phase was dried, filtered and concentrated, then re-dissolved in DCM and applied to a short plug of silica gel. The gel was washed with DCM and the washings were concentrated. The residue was taken up in ether and washed with 1.0M hydrochloric acid. The acidic water phase was made basic with 2.0M sodium hydroxide and the product was extracted back into ether. The combined ether phases were washed with brine, dried, filtered and concentrated to give 0.28 g (50%) of 5-bromo-2-cyclopropylpyridine as a yellow oil.

LC-MS m/z 197.9/199.9 (M+1);

$^1$H-NMR (CDCl$_3$) δ 8.48 (d, 1H), 7.63 (dd, 1H), 7.04 (d, 1H), 1.99 (m, 1H), 1.03-0.98 (m, 4H) ppm.

5-Bromo-2-cyclopropylpyridine (0.21 g, 1.1 mmol), bis(pinacolato)diboron (0.31 g, 1.2 mmol) and potassium acetate (0.32 g, 3.2 mmol) were suspended in dioxane (10 mL). The slurry was degassed with argon for 10 minutes and then PdCl$_2$×dppf (0.026 g) was added. The reaction mixture was heated to 80° C. for 15 h and then, after cooling to RT, filtered through a Celite plug. The filtrate was concentrated to give a black oil that was dissolved in ether and extracted four times with 1.0M sodium hydroxide. The combined yellow water phases were cooled to 10° C., acidified with 2.5M hydrochloric acid to pH 6.5 and then extracted repeatedly with ether. The combined organic phases were dried over anhydrous magnesium sulfate, filtered and concentrated to give 0.27 g (103%) of the title product as a yellow oil that slowly solidified. $^1$H-NMR suggested a purity of about 60-65% of the required product, the major contaminant being pinacolborane. The crude material was used without further purification.

GC-MS m/z 245.2 (M+), 244.2 (M−1);
$^1$H-NMR (CDCl$_3$) δ 8.78 (br s, 1H), 7.93 (dd, 1H), 7.10 (d, 1H), 2.10 (m, 1H), 1.34 (s, 12H), 1.10-1.00 (m, 4H) ppm.

tert-Butyl 6-{[(trifluoromethyl)sulfonyl]oxy}-3,4-dihydro-2,7-naphthyridine-2(1H)-carboxylate Crude 3-methoxy-2,7-naphthyridine (prepared from 4.4 mmoles of 6-methoxy-4-[(trimethylsilyl)ethynyl]nicotinaldehyde) was hydrogenated (30 psi pressure) at RT over PtO$_2$ (approx. 0.1 g) in HOAc (25 mL) for 2.5 h. The solution was filtered through a Celite pad and the clear filtrate was concentrated by freeze-drying to give crude 6-methoxy-1,2,3,4-tetrahydro-2,7-naphthyridine as the acetate.

LC-MS m/z 165 (M+1).

This material was refluxed in 48% hydrobromic acid for 10 h. The volatiles were evaporated and the residue was dried under vacuum at 45° C. to give crude 5,6,7,8-tetrahydro-2,7-naphthyridin-3-ol hydrobromide (approximately 0.70 g).

LC-MS m/z 151 (M+1).

This material (about 4.8 mmol) was dissolved in water (13 mL) and treated with THF (33 mL), Et$_3$N (0.85 mL, 6.0 mmol) and BOC-anhydride (1.6 g, 7.3 mmol) at RT. After stirring at the same temperature for 6 h the solution was concentrated to one third of its original volume and the residue was taken up in water and extracted three times with EtOAc. The combined organic phases were dried, filtered and concentrated to give 0.80 g (67% crude yield) of tert-butyl 6-hydroxy-3,4-dihydro-2,7-naphthyridine-2(1H)-carboxylate as a white solid.

LC-MS m/z 251 (M+1), 195 (M−55).

This material (about 5.4 mmoles) was dissolved in a two-phase system of toluene (20 mL) and 30% aqueous tripotassium orthophosphate (20 mL), and treated with triflic anhydride (1.6 mL, 6.8 mmol) at 4° C. [*Org. Lett.* 2002, 4(26), 4717-4718]. The ice-bath was removed, the stirring continued for 2 h at RT after which the two phases were separated. The aqueous phase was washed once with toluene. The combined organic phases were washed with brine, dried and concentrated. Purification by column chromatography with EtOAc-heptanes (2:1) as eluent gave 0.45 g (17% yield) of the title product.

LC-MS m/z 383 (M+1), 283 (M−99).

3-Methoxy-2,7-naphthridine

To a stirred solution of N,N,N'-trimethylethylenediamine (1.9 mL, 15 mmol) in anhydrous THF (65 mL) under argon at −70° C. was slowly added 1.6M n-BuLi in hexanes (9.0 mL, 14 mmol). After stirring at −70° C. for 15 minutes, 6-methoxy-nicotinaldehyde (1.3 g, 9.8 mmol) was added dropwise. After the addition was complete, stirring was continued at −70° C. for another 15 minutes. Then 1.6M n-BuLi in hexanes (10 mL, 16 mmol) was added dropwise and stirring continued at −45° C. for 4 h. The solution was cooled to −70° C. and then a solution of iodine (3.0 g, 12 mmol) in anhydrous THF (25 mL) was added dropwise. When the addition was complete, stirring was continued at −70° C. for 30 minutes and then at RT for 3 h. The crude product was taken up in ether (40 mL) and washed successively with saturated ammonium chloride (2×40 mL) and 5% sodium thiosulfate (2×20 mL). The organic phase was dried, filtered and concentrated. Purification by column chromatography with EtOAc-heptanes (1:1) as eluent gave 0.41 g (15% yield) of 4-iodo-6-methoxynicotinaldehyde.

LC-MS m/z 264 (M+1);
$^1$H NMR (CDCl$_3$) δ 9.95 (s, 1H), 8.53 (s, 1H), 7.32 (s, 1H) and 3.98 (s, 3H) ppm.

4-Iodo-6-methoxynicotinaldehyde (0.41 g, 1.6 mmoles), trimethylsilylacetylene (0.35 mL, 2.8 mmol), PdCl$_2$(PPh$_3$)$_2$ (catalytic amount), CuI (catalytic amount), triethylamine (2 mL) and THF (10 mL) were stirred at 60° C. for 2 h. The volatiles were evaporated and the residue was taken up in water and extracted with ether. The organic phase was dried, filtered and concentrated. Purification by column chromatography with EtOAc-heptanes (1:3) as eluent gave 0.25 g (68% yield) of 6-methoxy-4-[(trimethylsilyl)ethynyl]nicotinaldehyde.

LC-MS m/z 234 (M+1);
$^1$H NMR (CDCl$_3$) δ 10.4 (s, 1H), 8.73 (s, 1H), 6.84 (s, 1H), 4.03 (s, 3H) and 0.30 (s, 9H) ppm.

6-Methoxy-4-[(trimethylsilyl)ethynyl]-nicotinaldehyde (0.25 g, 1.1 mmol) and 7M ammonia in MeOH (5 mL) were stirred in a sealed vial at 80° C. overnight. The solution was concentrated, taken up in saturated sodium carbonate and extracted with ether. The organic phase was dried, filtered and concentrated to give 0.20 g of the title product.

GC-MS m/z 160 (M$^+$);
$^1$H NMR (CDCl$_3$) δ 9.41 (s, 1H), 9.27 (s, 1H), 8.47 (d, 1H), 7.64 (d, 1H), 7.03 (s, 1H) and 4.12 (s, 3H) ppm.

EXAMPLE 3

(5S)-5-({[6-(2-Cyclopropylpyrimidin-5-yl)-3,4-dihydro-2,7-naphthyridin-2(1H)-yl]sulfonyl}methyl)-5-methylimidazolidine-2,4-dione To a stirred solution of 6-(2-cyclopropylpyrimidin-5-yl)-1,2,3,4-tetrahydro-2,7-naphthyridine hydrochloride (0.12 g, 0.42 mmol) in DCM (10 mL) was added TEA (0.12 mL, 0.84 mmol) followed by the dropwise addition of [(4S)-4-methyl-2,5-dioxoimidazolidin-4-yl]methanesulfonyl chloride (0.090 g, 0.40 mmol) in THF (10 mL) at −10° C. The mixture was stirred at RT overnight, concentrated, taken up in water (10 mL) and extracted four times with EtOAc. The combined organic phases were dried, filtered and concentrated. Purification by prep-HPLC gave 0.12 g (64%) of the title compound as a white solid.

LC-MS m/z 442.9 (M+1);
$^1$H NMR (CD$_3$OD) δ 9.05 (s, 2H), 8.43 (s, 1H), 7.81 (s, 1H), 4.63 (s, 2H), 3.40 (t, 2H), 3.38 (q, 2H), 3.00 (t, 2H), 2.20 (m, 1H), 1.40 (s, 3H) and 1.05 (m, 4H) ppm.

EXAMPLE 4

(5S)-5-({[6-(2-Cyclopropylpyrimidin-5-yl)-3,4-dihydro-2,7-naphthyridin-2(1H)-yl]sulfonyl}methyl)-5-ethylimidazolidine-2,4-dione

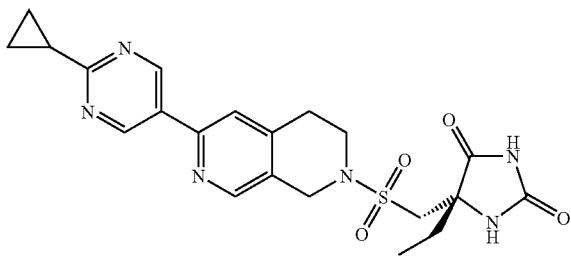

The title compound was prepared by the general method of Example 3 but using [(4S)-4-ethyl-2,5-dioxoimidazolidin-4-yl]methane-sulfonyl chloride.

LC-MS m/z 457 (M+1).

The starting materials were prepared as follows:

6-(2-Cyclopropylpyrimidin-5-yl)-1,2,3,4-tetrahydro-2,7-naphthridine hydrochloride A mixture of 2-tert-butyl-6-(2-cyclopropylpyrimidin-5-yl)-1,2,3,4-tetrahydro-2,7-naphthyridine (0.12 g, 0.39 mmol), 1-chloroethyl chloroformate (1.0 mL, 5.8 mmol) and toluene (10 mL) was refluxed for 4 h under protection from moisture (calcium chloride tube). After concentration to dryness, the dark residue was taken up in MeOH (10 mL) and refluxed for 3 h more. Charcoal (1 g) was added and refluxing continued for 20 minutes. Then the mixture was filtered through Celite and the clear filtrate was concentrated to give the title compound (0.12 g) as a solid.

LC-MS m/z 253 (M+1);

$^1$H NMR (CDCl$_3$) δ 9.22 (s, 2H), 8.57 (s, 1H), 7.98 (s, 1H), 4.41 (s, 2H), 3.45 (t, 2H), 2.44 (m, 2H), 2.32 (m, 1H) and 1.21 (m, 4H) ppm.

2-tert-Butyl-6-(2-cyclopropylpyrimidin-5-yl)-1,2,3,4-tetrahydro-2,7-naphthyridine To a stirred and cold (4° C.) solution of 2-tert-butyl-6-hydroxy-1,2,3,4-tetrahydro-2,7-naphthyridine (0.15 g, 0.73 mmol) in pyridine (5.0 mL) was slowly added triflic anhydride (0.14 mL, 0.80 mmol). When the addition was complete, the mixture was stirred at 4° C. for 30 minutes, quenched with 5% potassium carbonate solution (10 mL) and extracted four times with DCM. The combined organic phases were dried, filtered and concentrated to give a crude product. Column chromatography with EtOH-TBME (1:9) as eluent gave 0.30 g of the crude triflate as an oil.

LC-MS m/z 339.2 (M+1).

The triflate was dissolved in dioxane (10 mL) and anhydrous potassium acetate (0.43 g, 4.5 mmol), 2-cyclopropylpyrimidine-4-boronic acid (0.14 g, 0.89 mmol) and PdCl$_2$×dppf (0.0050 g) were added. The mixture was degassed with argon, sealed and stirred at 90° C. overnight. After cooling, the solution was taken up in water (20 mL) and extracted three is times with EtOAc. The combined organic phases were washed with brine, dried, filtered and concentrated. Column chromatography EtOH-TBME (1:9) and TBME-EtOH-TEA (20:2:1) gave 0.12 g (53% from two steps) of the title compound as a light brown solid.

LC-MS m/z 309 (M+1);

$^1$H NMR (CDCl$_3$) 9.05 (s, 2H), 8.45 (s, 1H), 7.38 (s, 1H), 3.97 (m, 2H), 2.95 (m, 4H), 2.00 (m, 1H), 1.21 (s, 9H), 1.11 (dt, 2H) and 1.09 (dt, 2H) ppm.

2-tert-Butyl-6-hydroxy-1,2,3,4-tetrahydro-2,7-naphthyridine

A solution of 2-tert-butyl-6-methoxy-1,2,3,4-tetrahydro-2,7-naphthyridine (5.1 g, 23 mmol) and 45% hydrobromic acid in acetic acid (70 mL) was heated in a sealed tube at 100° C. for 1 h, cooled to RT and concentrated. The residue was dissolved carefully in 20% potassium carbonate solution (100 mL) and extracted four times with EtOAc. The combined organic phases were dried, filtered and concentrated. Recrystallisation from TBME-hexanes gave 3.7 g (77%) of the title compound as a white solid.

LC-MS m/z 207 (+1);

$^1$H NMR (CDCl$_3$) δ 7.21 (s, 1H), 6.35 (s, 1H), 4.77 (m, 2H), 4.11 (m's, 4H) and 1.31 (s, 9H) ppm.

2-Cyclopropylpyrimidine-4-boronic acid

The title compound was prepared from 4-bromo-2-cyclopropylpyrimidine (WO 00/066566) in 90% yield (25 mmol scale) following the procedure by Li et al. (*J. Org. Chem.* 2002, 67, 5394-5397). LC-MS suggested that the product was composed of the boronic acid and the trimeric anhydride (sym-boroxine).

LC-MS m/z 165 (M+1) and 439 (M+1).

2-tert-Butyl-6-methoxy-1,2,3,4-tetrahydro-2,7-naphthyridine

To a stirred solution of 2,2,6,6-tetramethylpiperidine (9.0 mL, 60 mmol) in dry THF (300 mL) under argon at –20° C. was slowly added 1.6M n-BuLi in hexanes (40 mL, 60 mmol) while the temperature was kept at –20° C. After the addition was complete, stirring was continued at –20° C. for 40 min. Then a solution of tert-butyl-[(6-methoxy-4-methylpyridin-3-yl)methylene]amine (6.3 g, 30 mmol) in dry THF (100 mL) was added dropwise at –20° C. The mixture was stirred at –15 to –10° C. for 1.5 h and then cooled to –20° C. Anhydrous DMF (6.5 ml, 70 mmol) was added dropwise over five minutes and stirring continued at –10° C. for 1.5 h. Then glacial acetic acid (60 mL) in MeOH (250 ml) was added, followed by the portion-wise addition of sodium cyanoborohydride (2.3 g, 40 mmol) over five minutes. After stirring overnight, the solvent was evaporated and 20% potassium carbonate solution was added slowly to raise the pH to 9. The mixture was extracted four times with TBME. The combined organic phases were washed with brine, dried and concentrated to give a crude oil. Vacuum distillation gave 5.2 g (77%) of the title compound as a colourless oil, b.p. 105-106° C./0.5 mmHg.

GC-MS m/z 220.1 (M$^+$);

$^1$H NMR (CDCl$_3$) δ 7.90 (s, 1H), 6.55 (s, 1H), 3.95 (s, 3H), 3.81 (m, 3H), 2.95-2.90 (m, 3H) and 1.11 (s, 9H) ppm.

tert-Butyl-[(6-methoxy-4-methylpyridin-3-yl)methylene]amine

2-Methoxy-4-methylnicotinaldehyde (1.8 g, 12 mmol), tert-butylamine (15 mL), 3 Å molecular sieves (8 g) and dry DCM (10 mL) were mixed and allowed to stand at RT under protection from moisture (calcium chloride tube). After two days the mixture was filtered and the molecular sieves were washed several times with dry DCM. The combined washings were concentrated to give 2.2 g (89%) of the title compound as a crude oil that was used immediately in the next step.

$^1$H NMR (CDCl$_3$) δ 8.55 (br s, 1H), 8.50 (s, 1H), 6.50 (s, 1H), 3.96 (s, 3H), 2.50 (s, 3H) and 1.30 (s, 9H) ppm.

2-Methoxy-4-methylnicotinaldehyde

To a stirred solution of 5-bromo-2-methoxy-4-methylpyridine (2.6 g, 13 mmol) in dry THF (40 mL) under argon at −70° C. was added 1.6M n-BuLi in hexanes (8.1 mL, 14 mmol) over ten minutes. The mixture was stirred at −70° C. for 30 minutes and then anhydrous DMF (1.2 mL, 15 mmol) was added portion-wise at a rate that kept the temperature at −70° C. When the addition was complete, the mixture was stirred at −70° C. for 30 minutes and then at RT overnight. The reaction was quenched with 1M hydrochloric acid (40 mL) and then extracted three times with TBME. The combined organic phases were washed with brine, dried, filtered and concentrated. Column chromatography with TBME-light petroleum ether (1:1) as eluent gave 1.8 g (91%) of the title compound as pale yellow solid.

LC-MS m/z 152 (M+1);

$^1$H NMR (CDCl$_3$) δ 10.1 (s, 1H), 8.55 (s, 1H), 6.61 (s, 1H), 4.05 (s, 3H), 2.60 (s, 3H) ppm.

[(4S)-4-Ethyl-2,5-dioxoimidazolidin-4-yl]methanesulfonyl chloride

Prepared as described in WO 02/074767 for [(4S)-4-methyl-2,5-dioxoimidazolidin-4-yl]methanesulfonyl chloride.

EXAMPLE 5

(5S)-5-({[6-(2-Cyclopropylpyrimidin-5-yl)-3,4-dihydroisoquinolin-2(1H)-yl]sulfonyl}methyl)-5-ethylimidazolidine-2,4-dione

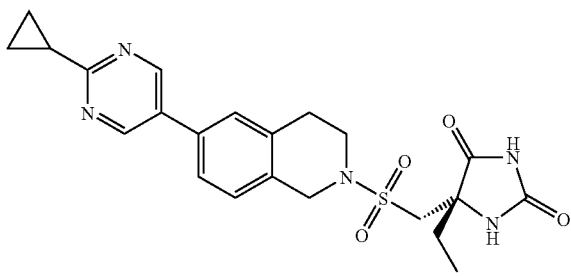

The title compound was prepared by chiral chromatographic resolution of (±)-5-({[6-(2-cyclopropylpyrimidin-5-yl)-3,4-dihydroisoquinolin-2(1H)-yl]sulfonyl}methyl)-5-ethylimidazolidine-2,4-dione using the procedure described in WO 02/074767.

Preparative Chromatographic Data:

| Chiracel OD-H column (L 25 cm, Ø 2 cm) Daicel Chemical Industries Ltd. | | |
|---|---|---|
| Eluent: 100% EtOH | Flow: 15 mL/min | Detection UV 254 nm. |

Analytical Chromatographic Data

| Chiralcel OD-H column (L 15 cm, Ø 0.46 cm) Daicel Chemical Industries Ltd. | | |
|---|---|---|
| Eluent: 100% EtOH | Flow: 0.30 mL/min | Detection UV 254/220 nm. |
| Retention time ($t_R$) - see below | | |

(S)-enantiomer ($t_R$ 13.0 Minutes)

$^1$H NMR (DMSO-d$_6$) δ 10.79 (br s, 1H), 8.94 (s, 2H), 7.97 (br s, 1H), 7.60-7.56 (m, 2H), 7.33-7.28 (m, 1H), 4.41 (s, 2H), 3.59-3.40 (m, 4H), 2.96 (t, J=6.2 Hz, 2H), 2.28-2.21 (m, 1H), 1.65 (q, J=7.6 Hz, 2H), 1.11-1.00 (m, 4H) and 0.78 (t, J=7.5 Hz, 3H) ppm.

(R)-enantiomer ($t_R$ 18.3 minutes)

$^1$H NMR (DMSO-d$_6$) δ 10.79 (br s, 1H), 8.94 (s, 2H), 7.97 (br s, 1H), 7.60-7.56 (m, 2H), 7.32-7.28 (m, 1H), 4.41 (s, 2H), 3.58-3.40 (m, 4H), 2.96 (t, J=6.2 Hz, 2H), 2.28-2.21 (m, 1H), 1.65 (q, J=7.6 Hz, 2H), 1.11-1.00 (m, 4H) and 0.78 (t, J=7.5 Hz, 3H) ppm.

(±)-5-({[6-(2-Cyclopropylpyrimidin-5-yl)-3,4-dihydroisoquinolin-2(1H)-yl]sulfonyl}methyl)-5-ethylimidazolidine-2,4-dione)

The title compound was prepared from 6-(2-cyclopropylpyrimidin-5-yl)-1,2,3,4-tetrahydroisoquinoline according to the procedure described in WO 02/074767.

LC-MS m/z 456 (M+1);

$^1$NMR (DMSO-d$_6$) δ 10.78 (br s, 1H), 8.94 (s, 2H), 8.03 (br s, 1H), 761-7.56 (m, 2H), 7.30 (d, J=8.5 Hz, 1H), 4.42 (s, 2H), 3.60-3.40 (m, 4H), 2.96 (t, J=6.2 Hz, 2H), 2.26-2.20 (m, 1H), 1.65 (q, J=7.2 Hz, 2H), 1.10-1.01 (m, 4H) and 0.78 (t, J=7.5 Hz, 3H) ppm.

EXAMPLE 6

(5S)-5-({[6-(2-Cyclobutylpyrimidin-5-yl)-3,4-dihydroisoquinolin-2(1H)-yl]sulfonyl}methyl)-5-methylimidazolidine-2,4-dione

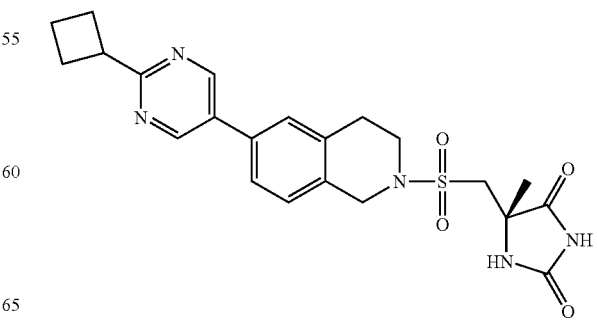

The title compound was prepared using the method described for Example 1.

LC-MS m/z 456 (M+1);

H₁NMR (300 MHz, DMSO-d₆) δ 1.31 (s, 3H), 1.83-2.12 (m, 2H), 2.26-2.45 (m, 4H), 2.96 (s, 2H), 3.19-3.55 (m, 4H), 3.78 (q, 1H), 4.43 (s, 2H), 6.92 (s, 1H), 7.32 (d, 1H), 7.60 (s, 2H), 9.04 (s, 2H), 10.81 (s, 1H) ppm.

The required starting materials were also prepared using the general methods described in Example 1:

1,1-Dimethylethyl 6-(2-cyclobutylpyrimidin-5-yl)-3,4-dihydroisoquinoline-2(1H)-carboxylate LC-MS m/z 366 (M+1);

¹H NMR (300 MHz, CDCl₃) δ 8.81 (s, 2H), 7.13-7.37 (m, 3H), 4.55 (d, 2H), 3.64 (t, 2H), 2.82-2.90 (m, 2H), 2.30-2.50 (m, 6H), 1.84-2.14 (m, 1H), 1.45 (s, 9H) ppm.

6-(2-Cyclobutylpyrimidin-5-yl)-1,2,3,4-tetrahydroisoquinolinium chloride

LC-MS m/z 266 (M+1);

Cyclobutyl(imino)methanaminium chloride

¹H NMR (300 MHz, DMSO-d₆) δ 1.69-1.84 (m, 1H), 1.86-2.05 (m, 2H), 2.08-2.32 (m, 3H), 3.29-3.42 (m, 1H), 8.85 (s, 4H) ppm.

5-Bromo-2-cyclobutylpyrimidine

GC-MS m/z 211/213 (M);

¹H NMR (300 MHz, CDCl₃) δ 1.88-2.17 (m, 2H), 2.36-2.46 (m, 4H), 3.78 (td, 1H), 8.72 (s, 2H) ppm.

EXAMPLE 7

(5S)-5-Methyl-5-({[6-[2-(1-methylcyclopropyl)pyrimidin-5-yl]-3,4 dihydroisoquinolin-2(1H)-yl]sulfonyl}methyl)imidazolidine-2,4-dione

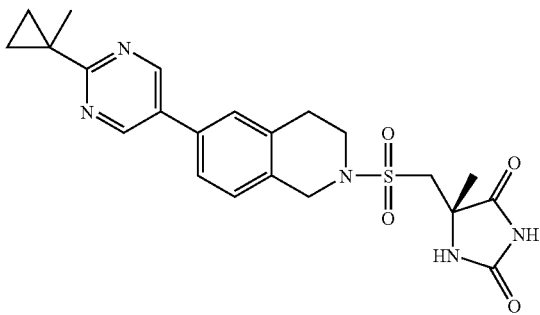

The title compound was prepared using the method described for Example 1.

LC-MS m/z 456 (M+1);

¹H NMR (300 MHz, DMSO-d₆) δ 0.94 (q, 2H), 1.30 (d, 2H), 1.34 (s, 3H), 1.54 (s, 3H), 2.96 (t, 2H), 3.40-3.62 (m, 4H), 4.42 (s, 2H), 7.31 (d, 1H), 7.58 (d, 2H), 8.06 (s, 1H), 8.97 (s, 2H), 10.77 (s, 1H) ppm.

The required starting materials were also prepared using the general methods described in Example 1:

6-[2-(1-Methylcyclopropyl)pyrimidin-5-yl]-1,2,3,4-tetrahydroisoquinolinium chloride LC-MS m/z 266 (M+1)

¹H NMR (300 MHz, DMSO-d₆) δ 0.94 (q, 2H), 1.30 (q, 2H), 1.53 (s, 3H), 2.96-3.14 (m, 2H), 3.29-3.42 (m, 2H), 4.18-4.32 (m, 2H), 5.81 (s, 1H), 7.15-7.27 (m, 1H), 7.36 (t, 1H), 7.63 (d, 1H), 8.98 (s, 2H), 9.85 (s, 1H) ppm.

Imino(1-methylcyclopropyl)methanaminium chloride

¹H NMR (300 MHz, DMSO-d₆) δ 0.46 (dd, 2H), 0.91 (q, 2H), 1.21 (s, 3H), 7.35 (s, 4H) ppm.

5-Bromo-2-(1-methylcyclopropyl)pyrimidine

LC-MS m/z 213/215 (M+1);

¹H NMR (399.988 MHz, CDCl₃) δ 0.93 (dd, 2H), 1.35 (dd, 2H), 1.54 (s, 3H), 8.59 (s, 2H) ppm.

EXAMPLE 8

(5S)-5-Cyclopropyl-5-({[6-(2-cyclopropylpyrimidin-5-yl)-3,4-dihydroisoquinolin-2(1H)-yl]sulfonyl}methyl)imidazolidine-2,4-dione

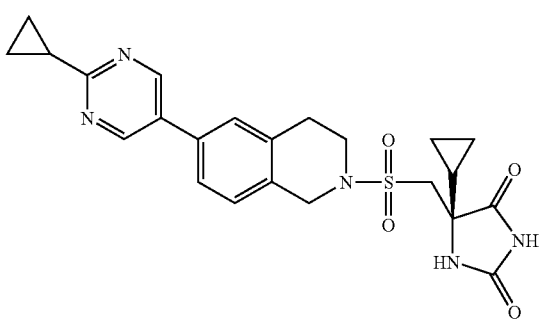

The title compound was prepared from 6-[2-(cyclopropyl)pyrimidin-5-yl]-1,2,3,4-tetrahydroisoquinoline and (4S)-(4-cyclopropyl-2,5-dioxoimidazolidin-4-yl)methanesulfonyl chloride using the general method described in Example 1.

LC-MS m/z 468 (M+1);

¹H NMR (400 MHz, DMSO-d₆) δ 0.18 (q, 1H), 0.33-0.56 (m, 3H), 1.02-1.17 (m, 5H), 2.24 (dd, 1H), 2.96 (t, 2H), 3.40-3.82 (m, 4H), 4.43 (s, 2H), 7.31 (t, 1H), 7.58 (d, 2H), 7.95 (s, 1H), 8.94 (s, 2H), 10.74 (s, 1H) ppm.

The required starting materials were prepared as follows:

2-Benzylsulfanyl-1-cyclopropyl-ethanone

Benzyl mercaptan (15.6 ml, 0.133 mol) was stirred in DCM (100 ml), triethylamine (20.5 ml, 0.146 mol) added, the mixture cooled in an ice/acetone bath and 2-bromo-1-cyclopropyl-ethanone, prepared as in WO 03/074495, (21.77 g, 0.133 mol) dissolved in DCM (100 ml) was added dropwise.

The mixture was stirred for 48 h, washed with water, then brine, dried over sodium sulphate and evaporated.

GC-MS m/z 206 (M);

$^1$H NMR (400 MHz, CDCl$_3$) δ 0.86-0.91 (m, 2H), 0.99-1.03 (m, 2H), 2.05-2.16 (m, 1H), 3.22 (s, 2H), 3.64 (s, 2H), 7.18-7.31 (m, 5H) ppm.

This material was used without any further purification.

Benzylsulfanylmethyl-5-cyclopropyl-imidazolidine-2,4-dione

2-Benzylsulfanyl-1-cyclopropyl-ethanone (27.55 g, 0.133 mol) was dissolved in ethanol (250 ml) and dispensed into 20×40 ml vials. Sodium cyanide (6.52 g, 0.133 mol) and ammonium carbonate (64 g, 0.667 mol) were dissolved in water (250 ml) and divided into the vials, which were then sealed and heated at 90° C. for 5 h behind a safety screen. After cooling to room temperature, the contents of the vials were combined, TBME was added, and the mixture was washed with water (×2), brine (×1), and then dried over sodium sulphate. Evaporation then gave the crude product (16.5 g, 45%). This material was absorbed onto silica and chromatographed (5×9.5 cm column of silica) eluting with iso-hexane to 50% ethyl acetate:iso-hexane to yield the title compound (11.81 g, 32.1%).

LC-MS m/z 277 (M+1);

$^1$H NMR (400 MHz, CDCl$_3$) δ 0.23-0.59 (m, 4H), 1.12-1.19 (m, 1H), 2.87 (dd, 2H), 3.67-3.74 (m, 2H), 6.06 (s, 1H), 7.15-7.33 (m, 5H), 8.66 (s, 1H) ppm.

The isomers were separated on a Chiralpak AD semi-prep column.
Eluent: 65% Ethanol/35% iso-hexane
Concentration: 50 mg per ml
Injection volume: 2 ml
Run time: 21 mins Chiral analysis on a Chiralpak AD 25×0.46 cm column, 0.7 ml/min gave retention times of 8.9 and 11.5 min. The faster running isomer was used for further reactions.

$^1$H NMR (400 MHz, CDCl$_3$) δ 0.19-0.58 (m, 4H), 1.10-1.24 (m, 1H), 2.86 (dd, 2H), 3.62-3.78 (m, 2H), 5.87 (s, 1H), 7.16-7.34 (m, 5H), 8.51 (s, 1H) ppm.

(4S)-(4-Cyclopropyl-2,5-dioxoimidazolidin-4-yl) methanesulfonyl chloride

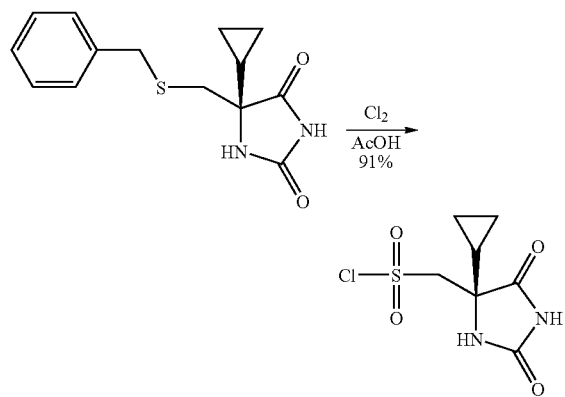

(5S)-Benzylsulfanylmethyl-5-cyclopropyl-imidazolidine-2,4-dione (770 mg, 2.78 mmol) was dissolved in 90% acetic acid (100 ml) and cooled in an ice water bath whilst chlorine gas was bubbled through for 10 minutes. The reaction mixture was freeze dried to give the title compound as a white solid (640 mg, 91%).

$^1$H NMR (400 MHz, THF) δ 0.37-0.65 (m, 4H), 1.25-1.33 (m, 1H), 4.62 (dd, 2H), 7.39 (s, 1H), 9.86 (s, 1H) ppm.

PHARMACOLOGICAL EXAMPLE

Isolated Enzyme Assays

MMP12

Recombinant human MMP12 catalytic domain may be expressed and purified as described by Parkar A. A. et al, (2000), Protein Expression and Purification, 20, 152. The purified enzyme can be used to monitor inhibitors of activity as follows: MMP12 (50 ng/ml final concentration) is incubated for 60 minutes at room temperature with the synthetic substrate Mca-Pro-Cha-Gly-Nva-His-Ala-Dpa-NH$_2$ (10 μM) in assay buffer (0.1M "Tris-HCl" (trade mark) buffer, pH 7.3 containing 0.1M NaCl, 20 mM CaCl$_2$, 0.020 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:

% Inhibition is equal to the [Fluorescence$_{plus\ inhibitor}$−Fluorescence$_{background}$] divided by the [Fluorescence$_{minus\ inhibitor}$−Fluorescence$_{background}$].

MMP8

Purified pro-MMP8 is purchased from Calbiochem. The enzyme (at 10 μg/ml) is activated by p-amino-phenyl-mercuric acetate (APMA) at 1 mM for 2.5 h, 35° C. The activated enzyme can be used to monitor inhibitors of activity as follows: MMP8 (200 ng/ml final concentration) is incubated for 90 minutes at 35° C. (80% H$_2$O) with the synthetic substrate Mca-Pro-Cha-Gly-Nva-His-Ala-Dpa-NH$_2$ (12.5 μM) in assay buffer (0.1 M "Tris-HCl" (trade mark) buffer, pH 7.5 containing 0.1M NaCl, 30 mM CaCl$_2$, 0.040 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:

% Inhibition is equal to the [Fluorescence$_{plus\ inhibitor}$−Fluorescence$_{background}$] divided by the [Fluorescence$_{minus\ inhibitor}$−Fluorescence$_{background}$].

MMP9

Recombinant human MMP9 catalytic domain was expressed and then purified by Zn chelate column chromatography followed by hydroxamate affinity column chromatography. The enzyme can be used to monitor inhibitors of activity as follows: MMP9 (5 ng/ml final concentration) is incubated for 30 minutes at RT with the synthetic substrate Mca-Pro-Cha-Gly-Nva-His-Ala-Dpa-NH$_2$ (5 μM) in assay buffer (0.1M "Tris-HCl" (trade mark) buffer, pH 7.3 containing 0.1M NaCl, 20 mM CaCl$_2$, 0.020 mM ZnCl and 0.05%

(w/v) "Brij 35" (trade mark) detergent) in the presence (10 concentrations) or absence of inhibitors. Activity is determined by measuring the fluorescence at µex 320 nm and µem 405 nm. Percent inhibition is calculated as follows:

% Inhibition is equal to the [Fluorescence$_{plus\ inhibitor}$−Fluorescence$_{background}$] divided by the [Fluorescence$_{minus\ inhibitor}$−Fluorescence$_{background}$].

MMP14

Recombinant human MMP14 catalytic domain may be expressed and purified as described by Parkar A. A. et al, (2000), Protein Expression and Purification, 20, 152. The purified enzyme can be used to monitor inhibitors of activity as follows: MMP14 (10 ng/ml final concentration) is incubated for 60 minutes at room temperature with the synthetic substrate Mca-Pro-Cha-Gly-Nva-His-Ala-Dpa-NH$_2$ (10 µM) in assay buffer (0.1M "Tris-HCl" (trade mark) buffer, pH 7.5 containing 0.1M NaCl, 20 mM CaCl$_2$, 0.020 mM ZnCl and 0.05% (w/v) "Brij 35" (trade mark) detergent) in the presence (5 concentrations) or absence of inhibitors. Activity is determined by measuring the fluorescence at λex 320 nm and λem 405 nm. Percent inhibition is calculated as follows: % Inhibition is equal to the [Fluorescence$_{plus\ inhibitor}$−Fluorescence$_{background}$] divided by the [Fluorescence$_{minus\ inhibitor}$−Fluorescence$_{background}$].

A protocol for testing against other matrix metalloproteinases, including MMP9, using expressed and purified pro NMP is described, for instance, by C. Graham Knight et al., (1992) FEBS Lett., 296(3), 263-266.

MMP19

Recombinant human MMP19 catalytic domain may be expressed and purified as described by Parkar A. A. et al, (2000), Protein Expression and Purification, 20:152. The purified enzyme can be used to monitor inhibitors of activity as follows: MMP19 (40 ng/ml final concentration) is incubated for 120 minutes at 35° C. with the synthetic substrate Mca-Pro-Leu-Ala-Nva-Dpa-Ala-Arg-NH$_2$ (5 µM) in assay buffer (0.1M "Tris-HCl" (trade mark) buffer, pH 7.3 containing 0.1M NaCl, 20 mM CaCl$_2$, 0.020 nM ZnCl and 0.05% (w/v) "Brij 35" (trade mark) detergent) in the presence (5 concentrations) or absence of inhibitors. Activity is determined by measuring the fluorescence at λex 320 nm and λem 405 nm. Percent inhibition is calculated as follows: % Inhibition is equal to the [Fluorescence$_{plus\ inhibitor}$−Fluorescence$_{background}$] divided by the [Fluorescence$_{minus\ inhibitor}$−Fluorescence$_{background}$].

The following table shows data for a representative selection of the compounds of the present invention.

TABLE

| Compound | hMMP12 IC$_{50}$ (nM) | hMMP9 IC$_{50}$ (nM) | hMMP8 IC$_{50}$ (nM) | hMMP14 IC$_{50}$ (nM) | hMMP19 IC$_{50}$ (nM) |
|---|---|---|---|---|---|
| Example 1 | 8.78 | 10.1 | 3050 | >10000 | >10000 |
| Example 2 | 26.6 | 21.5 | 2470 | >10000 | >10000 |
| Example 5 | 6.9 | 3.8 | 1310 | 8810 | 3760 |

The invention claimed is:

1. A compound of formula (I) or a pharmaceutically acceptable salt thereof (I)

wherein
R$^1$ represents cyclobutyl or cyclopropyl; said cyclopropyl group being optionally further substituted by CH$_3$, CN or one or two fluoro atoms;
R$^2$ represents C1 to 3 alkyl or cyclopropyl; and
A, A$^1$ and B independently represent CH or N.

2. A compound according to claim 1, wherein R$^1$ represents cyclopropyl.

3. A compound according to claim 1, wherein R$^2$ represents methyl or ethyl.

4. A compound according to claim 1, wherein B$^1$ represents CH.

5. A compound according to claim 1, wherein A and A$^1$ each represent N.

6. A compound according to claim 1 which is selected from the group consisting of:
(5S)-5-({[6-(2-cyclopropylpyrimidin-5-yl)-3,4-dihydroisoquinolin-2(1H)-yl]sulfonyl}methyl)-5-methylimidazolidine-2,4-dione;
(5S)-5-({[6-(6-cyclopropylpyridin-3-yl)-3,4-dihydro-2,7-naphthyridin-2(1H)-yl]sulfonyl}methyl)-5-methylimidazolidine-2,4-dione;
(5S)-5-({[6-(2-cyclopropylpyrimidin-5-yl)-3,4-dihydro-2,7-naphthyridin-2(1H)-yl]sulfonyl}methyl)-5-methylimidazolidine-2,4-dione;
(5S)-5-({[6-(2-cyclopropylpyrimidin-5-yl)-3,4-dihydro-2,7-naphthyridin-2(1H)-yl]sulfonyl}methyl)-5-ethylimidazolidine-2,4-dione;
(5S)-5-({[6-(2-cyclopropylpyrimidin-5-yl)-3,4-dihydroisoquinolin-2(1H)-yl]sulfonyl}methyl)-5-ethylimidazolidine-2,4-dione;
(5S)-5-({[6-(2-cyclobutylpyrimidin-5-yl)-3,4-dihydroisoquinolin-2(1H)-yl]sulfonyl}methyl)-5-methylimidazolidine-2,4-dione;
(5S)-5-methyl-5-({[6-[2-(1-methylcyclopropyl)pyrimidin-5-yl]-3,4-dihydroisoquinolin-2(1H)-yl]sulfonyl}methyl)imidazolidine-2,4-dione;
(5S)-5-Cyclopropyl-5-({[6-(2-cyclopropylpyrimidin-5-yl)-3,4-dihydroisoquinolin-2(1H)-yl]sulfonyl}methyl)imidazolidine-2,4-dione;
and pharmaceutically acceptable salts thereof.

7. A pharmaceutical composition comprising a compound of formula (I) or a pharmaceutically acceptable salt thereof as claimed in claim 1 in association with a pharmaceutically acceptable adjuvant, diluent or carrier.

8. A method of treating asthma, which comprises administering to a patient a therapeutically effective amount of a compound of formula (I) or a pharmaceutically acceptable salt thereof:

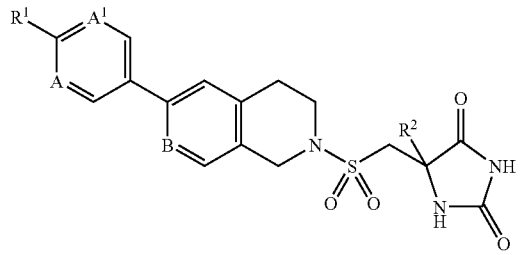

wherein
$R^1$ represents cyclobutyl or cyclopropyl; said cyclopropyl group being optionally further substituted by $CH_3$, CN or one or two fluoro atoms;
$R^2$ represents C1 to 3 alkyl or cyclopropyl; and
A, $A^1$ and B independently represent CH or N.

9. A method of treating chronic obstructive pulmonary disease, which comprises administering to a patient a therapeutically effective amount of a compound of formula (I) or a pharmaceutically acceptable salt thereof:

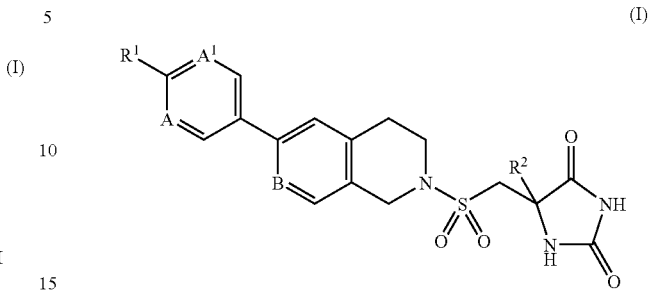

wherein
$R^1$ represents cyclobutyl or cyclopropyl; said cyclopropyl group being optionally further substituted by $CH_3$, CN or one or two fluoro atoms;
$R^2$ represents C1 to 3 alkyl or cyclopropyl; and
A, $A^1$ and B independently represent CH or N.

* * * * *

UNITED STATES PATENT AND TRADEMARK OFFICE
CERTIFICATE OF CORRECTION

PATENT NO.        : 7,655,664 B2                                    Page 1 of 1
APPLICATION NO.   : 11/721586
DATED             : February 2, 2010
INVENTOR(S)       : Balint Gabos et al.

It is certified that error appears in the above-identified patent and that said Letters Patent is hereby corrected as shown below:

Column 33, line 22, "Cl," should read -- C1 --.

Signed and Sealed this

Twelfth Day of October, 2010

David J. Kappos
*Director of the United States Patent and Trademark Office*